United States Patent [19]

Shibasaki et al.

[11] Patent Number: 6,090,969
[45] Date of Patent: *Jul. 18, 2000

[54] PROCESS FOR THE PREPARATION OF AN ASYMMETRIC COMPOUND USING A METAL COMPLEX

[75] Inventors: Masakatsu Shibasaki, Mitaka; Hiroaki Sasai, Chiba; Takayoshi Arai, Tokyo, all of Japan

[73] Assignee: Nagase and Co., Ltd., Osaka, Japan

[ * ] Notice: This patent is subject to a terminal disclaimer.

[21] Appl. No.: 09/149,735

[22] Filed: Sep. 8, 1998

Related U.S. Application Data

[63] Continuation of application No. 08/913,784, Dec. 5, 1997, Pat. No. 5,847,186.

[30] Foreign Application Priority Data

Mar. 22, 1995 [JP] Japan ...................................... 7-63091
Mar. 4, 1996 [JP] Japan ...................................... 8-46106

[51] Int. Cl.[7] .......................... C07C 255/00; C07C 41/00; C07C 39/14
[52] U.S. Cl. ........................... 558/423; 568/632; 568/735
[58] Field of Search ............................ 558/423; 568/632, 568/735

[56] References Cited

U.S. PATENT DOCUMENTS 4,965,398 10/1990 Mikami et al. ........................... 560/60
5,847,186 12/1998 Shibasaki et al. ....................... 558/120

FOREIGN PATENT DOCUMENTS 7-265709 10/1995 Japan ............................... B01J 31/22

OTHER PUBLICATIONS

H. Sasi et al., *J. Am. Chem. Soc.*, 114, p. 4418 (1992).
M. Shibasaki et al., *J. Synth. Org. Chem., Japan*, 51, p. 972 (1993).
H. Sasai et al., *J. Am. Chem. Soc.*, 116, p. 1571 (1994).
H. Sasai et al., *J. Org. Chem.*, 60, p. 6656 (1995).
T. Yokomatsu et al., *Tetrahedron: Asymmetry*, 4, p. 1783 (1993).

N. P. Rath, *Terahedron lett.*, 35 (2), p. 227 (1994).
Arai et al., "A new multifunctional heterobimetallic asymmetric catalyst for Michael additions and tandem Michael–aldol reactions," *Angewandte Chemie International Edition*, vol. 35, No. 1, Jan. 1996, pp. 104–106.
Noyori et al., "Rational designing of efficient chiral reducing agents, highly enantioselective reduction of aromatic ketones by binaphthol–modified lithium aluminum hydride reagents, " *J. Am. Chem. Soc.*, vol. 106, No. 22, Oct. 31 1984, pp. 6709–6716.

*Primary Examiner*—Johann Richter
*Assistant Examiner*—Joseph Murray
*Attorney, Agent, or Firm*—Marshall, O'Toole, Gerstein, Murray & Borun

[57] ABSTRACT

A process for producing an asymmetric compound using a metal complex containing no rare earth metal element is disclosed. The process affords an optically active compound having high optical purity. Optically active binaphthol having the chemical formula

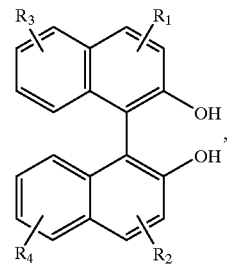

and lithium aluminum hydride are reacted, or the optically active binaphthol, a dialkyl aluminum hydride, and a base containing an alkali metal (or a base containing alkaline earth metal) are reacted to prepare a metal complex comprising optically active binaphthol, aluminum, and alkali metal (or alkaline earth metal). This metal complex can be used as a catalyst to perform an asymmetric Michael reaction, an asymmetric phosphonylation reaction, or the like, to obtain, in a high yield, an asymmetric compound having high optical purity.

10 Claims, No Drawings

PROCESS FOR THE PREPARATION OF AN ASYMMETRIC COMPOUND USING A METAL COMPLEX

CROSS-REFERENCE TO RELATED APPLICATION

This application is a continuation of application Ser. No. 08/913,784, filed on Dec. 5, 1997, now U.S. Pat. No. 5,847,186.

FIELD OF THE INVENTION

The present invention relates to a metal complex which can be used in the preparation of an asymmetric compound useful in the fields of medicines, agricultural chemicals, perfumes, liquid crystals, and the like. More particularly, it relates to a metal complex by which an optically active reaction product having high optical purity can be obtained in high yield when it is used as a catalyst for asymmetric Michael addition reaction, asymmetric hydrophosphonylation reaction, or the like, as well as a process for producing an asymmetric compound using a solution of the metal complex.

BACKGROUND OF THE INVENTION

The present inventors previously studied an asymmetric synthesis reaction using a metal complex catalyst of a rare earth metal element and, as a result, found that a metal complex prepared by a method of mixing lanthanum chloride ($LaCl_3$) and optically active dilithium binaphthoxide in tetrahydrofuran and adding water and sodium hydroxide thereto, or by a method of successively adding optically active binaphthol, water, and lithium chloride to a solution of $La_3(O\text{-}tC_4H_9)_9$ (lanthanum t-butoxide) in tetrahydrofuran containing sodium tert-butoxide, can catalyze an asymmetric nitroaldol reaction to afford a nitroaldol product having high optical purity (*J. Am. Chem. Soc.*, Vol. 114, p. 4418 (1992)).

In addition, the present inventors revealed that a complex prepared by adding 1 mole equivalent of optically active binaphthol to $La(O\text{-}iC_3H_7)_3$ (lanthanum isopropoxide) can catalyze an asymmetric Michael reaction to afford a Michael adduct having high optical purity (*J. Synth. Org. Chem.*, Jpn., Vol. 51, p. 972 (1993); *J. Am. Chem. Soc.*, Vol. 116, p. 1571 (1994)).

Further, the present inventors found that a metal complex, i.e., La-K-Binol (LPB), can act as an effective catalyst in imine-hydrophosphonylating reaction to afford a hydrophosphonyl compound having high optical purity (*J. Org. Chem.*, Vol. 60, p. 6656 (1995)).

In addition, it was found that a metal complex, La-Li-Binol (LnLB), can act as an effective catalyst in an aldehyde-hydrophosphonylating reaction to afford an asymmetric hydrophosphonylated compound (Tetrahedron: *Asymmetry*, Vol. 4, p. 1783 (1993); Tetrahedron Lett., Vol. 35, p. 227 (1994)).

However, lanthanum, which is a rare earth metal element contained in the aforementioned metal complexes, is difficult to obtain and, thus, the development of metal complex catalysts without using a rare earth metal is desired. However, such metal complex catalysts are not yet known.

On the other hand, an asymmetric Michael reaction product and an asymmetric α-hydrophosphonylated compound are both known as useful asymmetric compound reaction products. Particularly, a hydroxy phosphorylated compound has potent bioactivity and is expected to act effectively as an enzyme inhibitor for a synthesis enzyme such as renin, EPSP synthase, HIV protease, and the like and, thus, the development of an optically selective process for synthesizing these asymmetric phosphorylated compounds is desired. However, even when the above metal complex, Ln—Li—Binol (LnLB), is used in this application, either optical purity or yield of the resulting phosphorylated compound is not satisfactory. In addition, a reaction at an extremely low temperature is inevitably required. Thus, the above application has suffered many unsolved problems as an industrial process for preparing the above compounds.

SUMMARY OF THE INVENTION

The present invention provides a metal complex, or a solution of the metal complex, that can be used as a catalyst in an asymmetric Michael reaction and in an asymmetric hydrophosphonylation reaction, contains no rare earth metal element, and can afford an optically active compound having high optical purity at high yield. The present invention also provides a process for producing an asymmetric compound by an asymmetric Michael reaction and an asymmetric hydrophosphonylation reaction using such the metal complex.

The present inventors further studied an asymmetric synthesis catalyst using optically active binaphthol and a derivative thereof and found that, although the chemical structure is not clear, a metal complex prepared using an aluminum compound, without using a rare earth metal compound, acts as an extremely effective catalyst in the asymmetric Michael reaction and the asymmetric hydrophosphonylation reaction, and produces, at high yield, a Michael adduct and an asymmetric hydrophosphonylated compound having high optical purity.

That is, a metal complex of the present invention is characterized by the fact that it can be obtained by reacting optically active binaphthol, or a derivative thereof, with an alkali metal aluminum hydride or an alkali metal aluminum hydride compound.

In addition, a metal complex of the present invention is characterized by the fact that it can be obtained by reacting optically active binaphthol, or a derivative thereof, with dialkylaluminum hydride, and a base containing an alkali metal or a base containing an alkaline earth metal.

As the optically active binaphthol or derivative thereof that can be used for preparing a metal complex of the present invention, a compound represented by the following general formula 1 can be used:

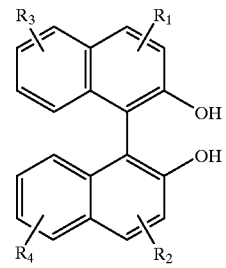

Chemical formula 1 wherein $R_1$, $R_2$, $R_3$, and $R_4$ are, independently, a group selected from the group consisting of a hydrogen atom, a lower alkyl group, a lower alkoxy group, halogen, cyano, and nitro. $R_1$ to $R_4$ can be the same or different from each other.

As the alkali metal aluminum hydride that can be used in preparation of a metal complex of the present invention, lithium aluminum hydride is a typical example. In addition, as the alkali metal aluminum hydride compound which can be used in preparation of a metal complex of the present invention, a compound that can be easily obtained, such as sodium-bis(methoxyethoxy) aluminum hydride, diisobutylaluminum hydride, and the like can be used. A preferable molar ratio of the optically active binaphthol or a derivative thereof and the alkali metal aluminum hydride in the preparation of a metal complex is in a range of 1–4:1, preferably 1.5–2.5:1, and more preferably 2:1.

As the dialkylaluminum hydride that can be used in the preparation of a metal complex of the present invention, there are diethylaluminum hydride, diisopropylaluminum hydride, diisobutylaluminum hydride, and the like. From among them, diisobutylaluminum hydride is preferably used.

In addition, as the base containing an alkali metal, there are sodium methylate, sodium ethylate, sodium isopropoxide, sodium tert-butoxide, lithium hydride, potassium hydride, sodium borohydride, lithium tert-butoxide, butyllithium, and the like. From among them, sodium tert-butoxide is preferably used. As the base containing an alkaline earth metal, barium tert-butoxide and the like can be used. An equivalent ratio of the optically active binaphthol or a derivative thereof, the dialkylaluminum hydride, and the base containing an alkali metal or an alkaline earth metal is 1–4:0.5–2:1. The use at an equivalent ratio of 1.5–2.5:0.5–1.5:1 is preferable and the use at an equivalent ratio of 2:1:1 is more preferable.

In addition, various organic solvents can be used in the preparation of the above metal complex. Particularly, ethereal solvents are preferable. From among them, tetrahydrofuran, diethyl ether, methyl tert-butyl ether, dioxane, and mixtures thereof are particularly preferable, although solvents such as toluene, hexane, heptane, and the like can be used. An organic solution, in which a metal complex is prepared, can be used as such for synthesizing an asymmetric compound without isolation of the metal complex therefrom.

The metal complex of the present invention, or a solution thereof, can be suitably used in an asymmetric Michael reaction and is particularly useful in a reaction of cyclopentenone or cyclohexenone with a malonic diester or an alkylmalonic diester.

Further, in asymmetric Michael reaction using the metal complex of the present invention or a solution thereof, an optically active compound having the following general formula 2 can be obtained by adding an aliphatic or an aromatic aldehyde thereto.

Chemical formula 2

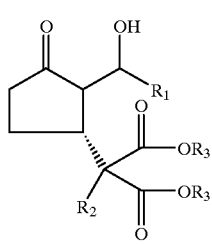

-continued

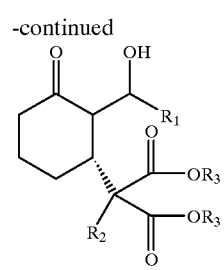

In the above formula, $R_1$ is a residue of an aliphatic compound or an aromatic compound, $R_2$ is hydrogen or an alkyl group, and $R_3$ is an alkyl group or an aralkyl group.

The metal complex of the present invention, or a solution thereof, can be suitably used in an asymmetric hydrophosphonylation reaction. A reaction solvent for performing this asymmetric hydrophosphonylation reaction is not limited to specified solvents, and preferably is benzene, toluene, or xylene.

The process for producing an asymmetric hydrophosphonylated compound of the present invention can be suitably used to obtain an asymmetric hydrophosphonylated compound shown by the following general formula 5 by reacting an aldehyde shown by the following general formula 3 with a phosphonic diester compound shown by the following general formula 4.

Chemical formula 3

$R_1$—⟨phenyl⟩—CHO

Chemical formula 4

$$H-\overset{O}{\underset{}{P}}(OR_2)_2$$

Chemical formula 5

$R_1$—⟨phenyl⟩—CH(OH)—*P(OR$_2$)$_2$=O

In the chemical formulas 3 to 5, $R_1$ is a hydrogen atom, a halogen atom, an alkyl group having 1–4 carbon atoms, an alkoxy group having 1–4 carbon atoms, a nitro group, an amino group, an alkylamino group, or a dialkylamino group, and $R_2$ is an alkyl group having 1–8 carbon atoms, an arylalkyl group, or a silylalkyl group. The symbol * represents an asymmetric carbon atom.

In addition, the process for producing an asymmetric hydrophosphonyl compound of the present invention can be suitably used to obtain an asymmetric hydrophosphonyl compound shown by the following general formula 8 by reacting an aldehyde shown by the following general formula 6 with a phosphonic diester compound shown by the following general formula 7.

Chemical formula 6

$R_3$\C=C/$R_5$ with CHO on one carbon and $R_4$ on the other

-continued

Chemical formula 7

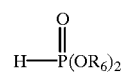

Chemical formula 8

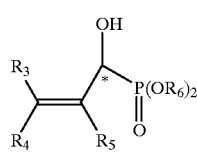

In the chemical formulas 6 to 8, $R_3$, $R_4$, and $R_5$ are, independently, a hydrogen atom, a phenyl group, a lower alkyl-substituted phenyl group, a lower alkoxy-substituted phenyl group, or an alkyl group or an alkoxy group each having 1–8 carbon atoms, or $R_3$ and $R_4$, or $R_4$ and $R_5$, can form a ring. In addition, $R_6$ is an alkyl group having 1–8 carbon atoms, an arylalkyl group, or a silylalkyl group, and the symbol * represents an asymmetric carbon atom.

Further, the process for producing an asymmetric hydrophosphonyl compound of the present invention can be suitably used to obtain an asymmetric hydrophosphonyl compound shown by the following general formula 11 by reacting an aldehyde shown by the following general formula 9 with a phosphonic diester compound shown by the following general formula 10.

Chemical formula 9

Chemical formula 10

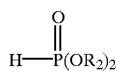

Chemical formula 11

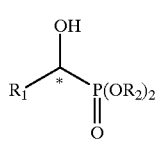

In the chemical formulas 9 to 11, $R_1$ is a linear or branched alkyl group having 1–8 carbon atoms, or a cyclic alkyl group having 3–10 carbon atoms. In addition, $R_2$ is an alkyl group having 1–8 carbon atoms, an arylalkyl group, or a silylalkyl group, and the symbol * represents an asymmetric carbon atom.

In the present invention, the asymmetric hydrophosphonylation reaction can be carried out at the temperature of −70° C. to 45° C. However, from a viewpoint of optical purity, the reaction temperature preferably is −20° C. to −60° C., more preferably −30° C. to −45° C., and most preferably −40° C.

In the asymmetric hydrophosphonylation reaction of the present invention, various organic solvents can be used. From among them, aromatic hydrocarbons such as xylene, toluene, benzene, and mixtures thereof are particularly preferable. However, aliphatic hydrocarbons, such as hexane, heptane, and the like, ether compounds, such as tetrahydrofuran, diethyl ether, methyl tert-butyl ether, dioxane, and the like can be used.

PREFERRED EMBODIMENTS OF THE PRESENT INVENTION

The following Examples illustrate a process for preparing a metal complex of the present invention, and a process for producing an asymmetric compound by an asymmetric Michael reaction and an asymmetric hydrophosphonylation reaction using the metal complex as a catalyst, but the present invention is not limited by these disclosures.

EXAMPLE 1

Preparation of Al—Li-(R)-binaphthol Complex

Lithium aluminum hydride (114 mg, 3.0 mmol) was dissolved in anhydrous tetrahydrofuran (15 ml) under an argon atmosphere. To this solution was added, dropwise, a solution of (R)-binaphthol in anhydrous tetrahydrofuran (1.72 g, 6.0 mmol/THF 15 ml) at 0C., which was stirred at room temperature for 12 hours. The supernatant was used as a solution of Al—Li-(R)-binaphthol complex in tetrahydrofuran (0.1 M).

EXAMPLE 2

Preparation of Al—Na-(R)-binaphthol Complex

To a solution of (R)-binaphthol in anhydrous tetrahydrofuran (0.1 M, 2.0 ml) was added, dropwise, a solution of diisobutylaluminium hydride in tetrahydrofuran (1.0 M, 0.1 ml) at 0° C., which was stirred for 15 minutes. Thereafter, a solution of sodium tertiary butoxide in tetrahydrofuran (0.8 M, 0.12 ml) was added thereto, which was stirred at room temperature for another 30 minutes to obtain a solution of Al—Na-(R)-binaphthol complex in tetrahydrofuran.

EXAMPLE 3

Preparation of Al—Ba-(R)-binaphthol Complex

To a solution of (R)-binaphthol in anhydrous tetrahydrofuran (0.1 M, 2.0 ml) was added a solution of diisobutylaluminum hydride in tetrahydrofuran (0.1 M, 0.1 ml) at 0° C., which was stirred for 15 minutes. Thereafter, a solution of barium dibenzyl malonate in tetrahydrofuran (1.0 M, 0.1 ml), which had been prepared by prereacting 2 equivalents of dibenzyl malonate and barium tertiary butoxide (Ba(O-tC$_4$H$_9$)$_2$), was added thereto, which was stirred at room temperature for another 30 minutes to obtain a solution of Al—Ba-(R)-binaphthol complex in tetrahydrofuran.

EXAMPLE 4

Preparation of Al—Li-(R)-6,6'-dibromobinaphthol

The same procedure as shown in Example 1 was used, except that (R)-6,6'-dibromobinaphthol (obtained from Kankyokagaku Center Co., Ltd.) was used in place of the (R)-binaphthol of Example 1 to afford Al—Li-(R)-6,6'-dibromobinaphthol. As Reference Example, a process for synthesizing (R)-6,6'-dibromobinaphthol is shown below.

REFERENCE EXAMPLE

Synthesis of (R)-6,6'-dibromobinaphthol (R)-binaphthol (750 mg, 2.6 mmol) was dissolved in 20 ml of methylene chloride, which was cooled to −78° C. To this solution was added, dropwise, bromine (0.32 ml, 6.3 mmol), which was stirred at −78° C. for 30 minutes and then at room temperature for 2 hours. After completion of the reaction, the reaction mixture was treated with sodium thiosulfate to obtain 6,6'-dibromobinaphthol (the following structural formula 12).

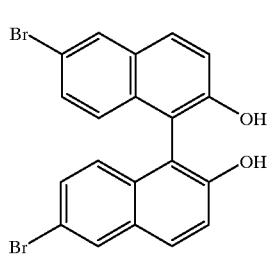

Chemical formula 12

EXAMPLE 5

Preparation of Al—Li-(R)-6,6'-dicyanobinaphthol

Preparation of 6,6'-dicyanobinaphthol (1) The reaction was carried out according to the same procedure as shown in Example 4, except that the purification step after treatment with sodium thiosulfate was omitted, to obtain crude 6,6'-dibromobinaphthol which was used in the next step without further purification.

(2) Crude 6,6'-dibromobinaphthol was dissolved in dimethylformamide (5 ml, abbreviated as DMF hereinafter). This solution was added to a suspension of sodium hydride (800 mg) in DMF (30 ml) under ice-cooling, which was stirred for 30 minutes. After methoxymethyl chloride (hereinafter abbreviated as MOMCl) (1.2 ml) was added thereto, the mixture was stirred at room temperature for 3 hours. The reaction solution was poured into water. The mixture was extracted with ethyl acetate, and the solvent was distilled of f to obtain crude Br-MOM protected compound (the following structural formula 13).

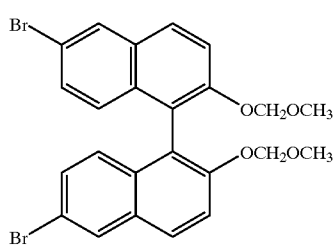

Chemical formula 13

(3) The crude Br-MOM protected compound obtained in the above step (2) was dissolved in benzene and azeotropic dehydration was carried out three times. Thereafter, the solution was dissolved in 30 ml of tetrahydrofuran (hereinafter abbreviated as THF), which was cooled to −78° C. under argon atmosphere. Then, n-butyllithium (4.3 ml, 1.05 equivalents to the Br-MOM protected compound) was added thereto to stir for 1 hour. Thereafter, 500 μl of dry DMF was added thereto to stir at room temperature for 5 hours. The reaction was poured into water, and the mixture was extracted with ethyl acetate, then the solvent was distilled off to obtain crude OHC-MOM protected compound (the following structural formula 14).

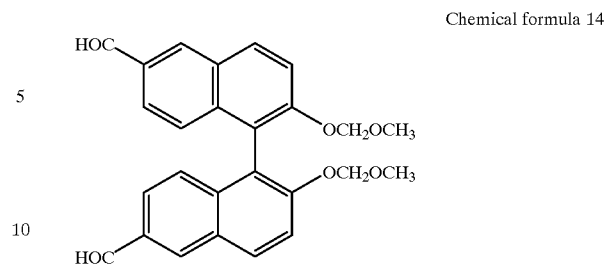

Chemical formula 14

The results of an analysis of this compound are shown in Table 1.

TABLE 1

| $^1$H NMR (CDCl$_3$) (δ) | 3.19(s, 6H), 5.13(d, J=7.0Hz, 2H), 5.23(d, J=7.0Hz, 2H), 7.27 (d, J=8.9Hz, 2H), 7.77 (d, J=8.9Hz, 4H), 8.20 (d, J=9.2Hz, 2H), 8.46(s, 2H), 10.20 (s, 2H) |
|---|---|

(4) The crude OHC-MOM protected compound obtained in the above step (3) was dissolved in methyl alcohol (80 ml), then sodium bicarbonate (10 g) and hydroxylamine hydrochloride (4.1 g) were added thereto. After stirring at room temperature for 1 hour, a majority of methyl alcohol was distilled off, and the remainder was poured into water. The mixture was extracted with ethyl acetate, and the combined extracts were concentrated to obtain a crude dioxime-MOM protected compound (the following structural formula 15). This compound was used in the next step without further purification.

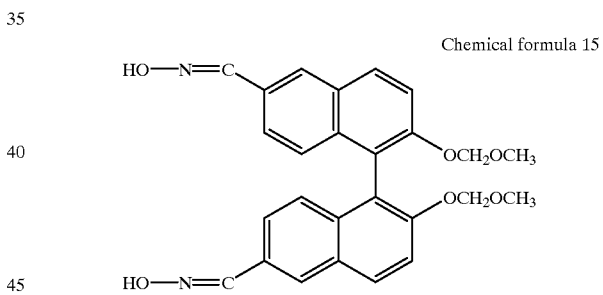

Chemical formula 15

The results of an analysis of this compound are shown in Table 2.

TABLE 2

| $^1$H NMR (CDCl$_3$) (δ) | 3.17(s, 6H), 5.00(d, J=7.2Hz, 2H), 5.10(d, J=6.9Hz, 2H), 7.12 (d, J=8.9Hz, 2H), 7.55 (dd, J=7.2, 1.6Hz, 2H), 7.60 (d, J=8.9Hz, 2H), 7.91 (d, J=1.4Hz, 2H), 7.97 (d, J=8.9Hz, 2H), 8.25(s, 2H) |
|---|---|

(5) The compound obtained in the above step (4) was suspended in 80 ml of methylene chloride, and 1,8-diazabicyclo[5.4.0.]undec-7-ene (DBU) (3.2 ml) was added thereto to complete dissolution. To this solution was added p-toluenesulfonyl chloride (2.0 g) at room temperature. After stirring at room temperature for 30 minutes, the mixture was poured into water. The mixture was extracted with ethyl acetate. The combined extracts were washed with aqueous sodium carbonate solution, and concentrated. The residue was purified by column chromatography (flash chromatography on silica (SiO$_2$)) to obtain dicyano-MOM protected compound (1.1 g (wet weight)) (the following structural formula 16).

Chemical formula 16

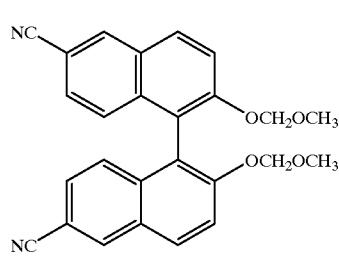

The results of an analysis of this compound are shown in Table 3.

TABLE 3

| $^1$H NMR (CDCl$_3$) (δ) | 3.12(s, 6H), 4.98(d, J=6.9Hz, 2H), 5.03(d, J=6.9Hz, 2H), 7.08 (d, J=8.9Hz, 2H), 7.20 (dd, J=1.7, 8.6Hz, 2H), 7.65 (d, J=8.9Hz, 2H), 7.97 (d, J=8.9Hz, 2H), 8.21(d, J=1.7Hz, 2H) |
|---|---|

(6) The dicyano-MOM protected compound obtained in the above step (5) was dissolved in a mixed solvent of THF (20 ml) and concentrated hydrochloric acid (15 ml). After stirring at room temperature for 2 hours. Completion of the reaction was confirmed by thin layer chromatography. The reaction solution was poured into water, and the mixture extracted with ethyl acetate. The combined extracts were concentrated. The residue was recrystallized from a mixed solvent of ethyl acetate/hexane (ethyl acetate:hexane=2:3 to 1:2) at room temperature to obtain (R)-6,6'-dicyanobinaphthol (500 mg).

The overall yield based on the raw material binaphthol used was 51%. Recrystallization was carried out again with the above mother liquor to obtain further 160 mg (yield 16%), with a total yield of 660 mg of (R)-6,6'-dicyanobinaphthol (the following structural formula 17). The overall yield from (R)-binaphthol was 67%.

Chemical formula 17

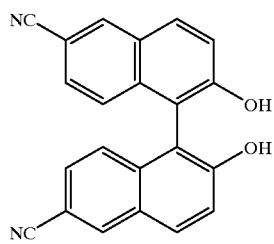

The results of an analysis of this compound are shown in Table 4.

TABLE 4

| $^1$H NMR (CDCl$_3$ + CD$_3$OD) (δ) | 7.13(d, J=8.0Hz, 2H), 7.46 (dd,J=1.7, 8.9Hz, 2H), 7.52 (d, J=8.9Hz, 2H), 8.07 (d, J=8.9Hz, 2H), 8.29 (d, J=1.7Hz, 2H) |
|---|---|

TABLE 4-continued

| Optical purity (HPLC analysis) | 99% e.e. HPLC analysis conditions: CHIRALPAK AD manufactured by Daicel Chemical Industries Co., Ltd., isopropanol/hexane = 1/9, detection: 254 nm, flow rate: 1.0 ml/min. |
|---|---|

(7) Preparation of Al—Li-(R)-6,6'-dicyanobinaphthol was achieved using the same procedure as shown in Example 1, except that the (R)-6,6'-dicyanobinaphthol obtained in the above steps (1) to (6) was used in place of (R)-binaphthol in Example 1 to afforded Al—Li-(R)-6,6'-dicyanobinaphthol.

EXAMPLE 6

Asymmetric Michael Reaction

Cyclohexenone (96 mg, 1.0 mmol) and dibenzyl malonate (250 mg, 1.0 mmol) were added to a solution of Al—Li-(R)-binaphthol complex in tetrahydrofuran (0.1 M, 1.0 ml), which was stirred at room temperature for 48 hours to carry out an asymmetric Michael reaction shown by the following chemical formula 18. The reaction was stopped by adding 1N hydrochloric acid (HCl) aqueous solution (3 ml) to the reaction solution. The mixture was extracted with ethyl acetate (15 ml×three times) and the combined extracts were dried over sodium sulfate (Na$_2$SO$_4$). The solvent was distilled off, and the residue was purified by flash column chromatography (acetone/hexane=1/10) using SiO$_2$ to obtain the Michael reaction product of a final compound in a yield of 91%.

Chemical formula 18

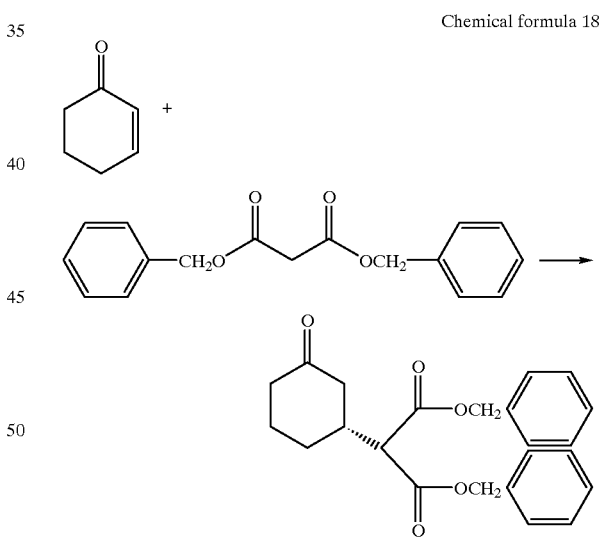

The results of an analysis of the reaction product in this Example are shown in Table 5.

TABLE 5

| IR (KBr) | 1740 cm$^{-1}$, 1261 cm$^{-1}$ |
|---|---|
| Melting point | 43° C. |
| $^1$H NMR (CDCl$_3$) (δ) | 1.46(dddd, J=3.0, 11.5, 11.5, -11.5Hz, 1H), 1.62(dddd, J=2.2, 2.4, -12.3, 12.3, 12.3Hz, 1H), 1.84–2.08 (m, 2H), 2.12–2.64(m, 5H), 3.41 (d, J=7.6Hz, 1H), 5.14(s, 2H), 5.16 |

TABLE 5-continued

| | |
|---|---|
| | (s, 2H), 7.25–7.36(m, 10H) |
| $^{13}$C NMR (CDCl$_3$) (δ) | 24.4, 28.6, 38.0, 40.9, 45.0, 56.6, 67.2, 128.2, 128.4, 128.5, 135.0, 167.4, 167.5, 209.3 |
| MS m/z | 289 (M$^+$ – Bn), 91 (base peak) |
| HRMS | for C$_{23}$H$_{24}$O$_5$ (M$^+$ – Bn) cal'd [C, 72.61.; H, 6.36], measured [C, 72.40; H, 6.13] |
| [α]$_p^{24}$ | +1.24° (c 1.02, CHCl$_3$) |
| Optical purity (HPLC analysis) | 98% e.e. HPLC analysis conditions: CHIRALPAK AS manufactured by Daicel Chemical Industries Co., Ltd., iso-propanol/hexane = 1/9, detection: 254 nm, flow rate: 1.0 ml/min. |

EXAMPLE 7

Asymmetric Michael Reaction

According to the same reaction conditions and operations as used in Example 6, cyclohexenone and diethyl malonate were subjected to the asymmetric Michael reaction to obtain the reaction product of the structural formula 19 in a yield of 87%.

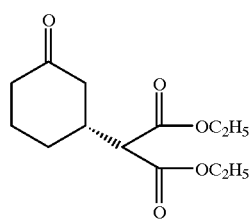

Chemical formula 19

An analysis was carried out on this reaction product in same manner as in Example 6, the results are shown in Table 6.

TABLE 6

| | |
|---|---|
| IR (KBr) | 1731 cm$^{-1}$, 1230 cm$^{-1}$ |
| $^1$H NMR (CDCl$_3$) (δ) | 1.20(t,J=7.3Hz, 3H), 1.21(t, J=-7.3Hz, 3H), 1.44(dddd, J=3.2, 12.1, -12.1, 12.1Hz, 1H), 1.62(ddddd, -J=3.2, 5.0, 12.1, 12.1, 12.1Hz, 1H), 1.83–1.95(m.1H), 1.95–2.07(m, 1H), 2.11–2.28(m, 2H), 2.28–2.54(m, 3H), 3.23(d, J=7.9Hz, 1H), 4.13 (q, J=7.3Hz, 2H), 4.14(q, J=7.3Hz, 2H) |
| $^{13}$C NMR (CDCl$_3$) (δ) | 14.0, 24.5, 28.7, 38.0, 40.9, 45.0, 56.8, 61.5, 167.7, 167.8, 209.6 |
| MS m/z | 256 (M$^+$), 211 (M$^+$ – OMe), 97 (base peak) |
| HRMS | for C$_{13}$H$_{20}$O$_5$ cal'd [C, 60.92; H, 7.87], measured [C, 60.64; H, 7.62] |
| [α]$_p^{24}$ | +3.33° (c 2.09, CHCl$_3$) |
| Optical purity (HPLC analysis) | 95% e.e. HPLC analysis conditions: CHIPALPAK AS manufactured by Daicel Chemical Industries Co., Ltd., iso-propanol/hexane = 1/9, detection: differential refraction, 254 nm, flow rate: 1.0 ml/min.) |

EXAMPLE 8

Asymmetric Michael Reaction

According to the same reaction conditions and operations as used in Example 6, cyclohexenone and dimethyl malonate were subjected to the asymmetric Michael reaction to obtain the reaction product of the structural formula 20 in a yield of 90%.

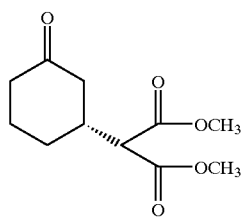

Chemical formula 20

The analysis was carried out on this reaction product in same manner as in Example 6, and the results are shown in Table 7.

TABLE 7

| | |
|---|---|
| IR (neat) | 1732 cm$^{-1}$, 1259 cm$^{-1}$ |
| $^1$H NMR (CDCl$_3$) (δ) | 1.46(dddd, J=2.6, 12.2, 12.2, 12.2Hz, -1H), 1.62(ddddd, J=2.6, 4.2, 12.2, 12.2–2, 12.2Hz, 1H), 1.86–1.97(m, 1H), 1.98–2.11(m, 1H), 2.15–2.31(m, 2H), 2.31–2.59(m, 3H), 3.32(d, J=7.9Hz, 1H), 3.71(s, 3H), 3.72(s.3H) |
| $^{13}$C NMR (CDCl$_3$) (δ) | 24.4, 28.7, 37.9, 38.0, 40.9, 45.0, 52.5, 56.5, 168.1, 168.2, 209.4 |
| MS m/z | 228 (M$^+$), 197(M$^{+ – OMe}$), 97 (base peak) |
| HRMS | for C$_{17}$H$_{16}$O$_5$ cal'd [C, 57.88; H, 7.07], measured [C, 57.70; H, 7.01] |
| [α]$_p^{24}$ | +3.73° (c 1.00, CHCl$_3$) |
| Optical purity (HPLC analysis) | 93% e.e. HPLC analysis conditions: CHIRALPAK AS manufactured by Daicel Chemical Industries Co., Ltd., iso-propanol/hexane = 1/9, detection: differential refraction, flow rate: 1.0 ml/min. |

EXAMPLE 9

Asymmetric Michael Reaction

According to the same reaction conditions and operations as used in Example 6, cyclopentenone and dibenzyl malonate were subjected to the asymmetric Michael reaction to obtain the reaction product of the structural formula 21 in a yield of 93%.

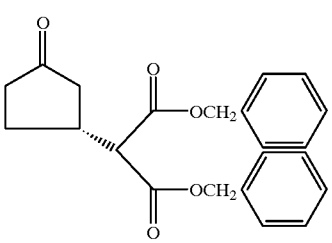

Chemical formula 21

The analysis was carried out on this reaction product in the same manner as in Example 6, and the results are obtained shown in Table 8.

TABLE 8

| | |
|---|---|
| IR (neat) | 1740 cm$^{-1}$, 1211 cm$^{-1}$ |
| $^1$H NMR (CDCl$_3$) (δ) | 1.51–1.72(m, 1H), 1.99(dd, J=11.2, -18.5Hz, 1H), 2.06–2.38(m, 3H), 2.45 (dd, J=7.9, 18.5Hz, 1H), 2.78–2.97(m, 1H), 3.45(d, J=9.6Hz, 1H), 5.14(s, 2H), 5.16 (s, 2H), 7.25–7.37(m, 10H) |
| $^{13}$C NMR (CDCl$_3$) (δ) | 27.4, 36.3, 38.1, 42.7, 56.4, 67.3, 67.3, 128.2, 128.5, 128.6, 135.0, 135.1, 167.7, 167.8, 216.9 |
| MS m/z | 275 (M$^+$ – Bn), 91 (base peak) |
| HRMS | for C$_{15}$H$_{15}$O$_5$ (M$^+$ – Bn) cal'd [275.0919] measured [275.0931] |
| [α]$_p^{24}$ | +35.0° (c 1.20, CHCl$_3$) |
| Optical purity (HPLC analysis) | 91% e.e. HPLC analysis conditions: CHIRALPAK AS manufactured by Daicel Chemical Industries Co., Ltd., isopropanol/hexane = 1/9, detection: 254 nm, flow rate: 1.0 ml/min. |

EXAMPLE 10

Asymmetric Michael Reaction

According to the same reaction conditions and operations as used in Example 6, cyclopentenone and diethyl methylmalonate were subjected to the asymmetric Michael reaction to obtain the reaction product of structural formula 22 in a yield of 84%.

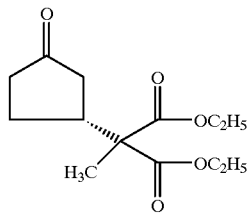

Chemical formula 22

The analysis was carried out on this reaction product in the same manner as in Example 2, and the results are obtained shown in Table 9.

TABLE 9

| | |
|---|---|
| IR (neat) | 2984 cm$^{-1}$, 1730 cm$^{-1}$, 1262 cm$^{-1}$ |
| $^1$H NMR (CDCl$_3$) (δ) | 1.25(t, J=7.0Hz, 3H), 1.26 (t, J=7.0Hz, 3H), 1.44(s, 1H), 1.60–1.84(m, 1H), 2.07–2.49 (m, 5H), 2.78–2.94(m, 1H), 4.19 (q, J=7Hz, 2H), 4.21(q, J=7Hz, 2H) |
| $^{13}$C NMR (CDCl$_3$) (δ) | 14.0, 17.8, 24.6, 38.5, 40.8, 41.4, 55.4, 61.4, 171.2, 171.3, 217.7 |
| MS m/z | 257 (M + 1), 288 (M + 1 – Et), 174 (base peak) |
| HRMS | for C$_{13}$H$_{20}$O$_5$ cal'd [C, 60.92; H, 7.87], measured [C, 60.66;H, 7.76] |
| [α]$_p^{24}$ | +54.9° (c 3.34, CHCl$_3$) |
| Optical purity (HPLC analysis) | 91% e.e. HPLC analysis conditions: CHIRALPAK AS manufactured by Daicel Chemical Industries Co., Ltd., isopropanol/hexane = 1/9, detection: 254 nm, flow rate: 1.0 ml/min. |

EXAMPLE 11

Asymmetric Michael Reaction

Cyclohexenone (96 mg, 1.0 mmol) and dibenzyl malonate (250 mg, 1.0 mmol) were added to the solution obtained in Example 2. After stirring at room temperature for 48 hours, 1N HCl aqueous solution (3 ml) was added to the reaction solution to stop the reaction. The mixture was extracted with ethyl acetate (15 ml×three times) and the combined extracts were dried over Na$_2$SO$_4$. The solvent was distilled from the reaction solution, and the residue was purified by flash column chromatography (acetone/hexane=1/10, on SiO$_2$) to obtain the Michael reaction product of a final compound in a yield of 44%. The optical purity by HPLC analysis was 97% e.e. (HPLC analysis conditions were the same as those in Example 6).

EXAMPLE 12

Asymmetric Michael Reaction

Cyclohexenone (96 mg, 1.0 mmol) and dibenzyl malonate (250 mg, 1.0 mmol) were added to the solution obtained in Example 3. After stirring at room temperature for 6 hours. A 1N HCl aqueous solution (3 ml) was added to the reaction solution to stop the reaction. The mixture was extracted with ethyl acetate (15 ml×three times) and the combined extracts were dried over Na$_2$SO$_4$. The solvent was distilled from the reaction solution, and the residue was purified by flash column chromatography (acetone/hexane=1/10, on SiO$_2$) to obtain the Michael reaction product of a final compound in a yield of 100%. The optical purity of the product was 87% e.e as analyzed by HPLC. (HPLC analysis conditions were the same as those in Example 6).

EXAMPLE 13

Three-component Combination Type Reaction

Cyclopentenone (84 mg, 1.0 mmol), diethyl methylmalonate (138 mg, 1.0 mmol), and hydrocinnamaldehyde (158 mg, 1.2 mmol) were added to a solution of Al—Li-(R)-binaphthol complex obtained in Example 1 (0.1 M, 1.0 ml). The stirring was continued at room temperature for 36 hours to carry out the reaction below.

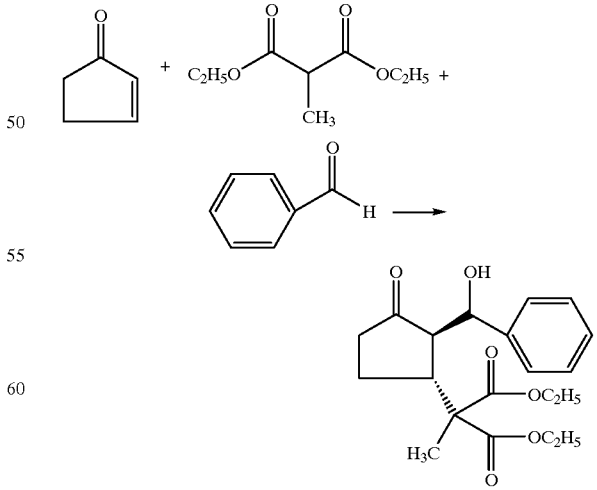

Chemical formula 23

After 1N HCl aqueous solution (3 ml) was added to this reaction solution to stop the reaction, the mixture was extracted with ethyl acetate (15 ml×three times). The combined extracts were dried over Na$_2$SO$_4$. After the solvent was distilled, the residue was purified by flash column chromatography (acetone/hexane=1/10, on SiO$_2$) to afford the three-component combination type reaction product of a final compound in a yield of 64%. An analysis was performed on this reaction product in same manner as in Example 6 to obtain the results shown in Table 10.

TABLE 10

| | |
|---|---|
| IR (neat) | 3518 cm$^{-1}$, 3085 cm$^{-1}$, 1728 cm$^{-1}$, 1253 cm$^1$ |
| $^1$H NMR (CDCl$_3$) (δ) | 1.19(t, J=7.0Hz, 3H), 1.22 (t, J=7.0Hz, 3H), 1.40(s, 3H), 1.68–1.87(m, 2H), 2.01–2.19(m, 2H), 2.24(t, J=8.4Hz, 2H), 2.35(dd, J=3.8, 6.3Hz, 1H), 2.57–2.70(m, 2H), 2.76–2.899(m, 1H), 2.97 (dt, J=6.3, 8.0Hz, 1H), 3.75 (dt, J=3.8, 9.6Hz, 1H), 4.06 (q, J=7.0Hz, 1H), 4.11 (q, J=7.0Hz, 1H), 4.13 (q, J=7.0Hz, 2H), 7.13–7.40(m, 5H) |
| $^{13}$C NMR (CDCl$_3$) (δ) | 13.9, 14.0, 18.6, 22.9, 32.5, 36.1, 38.5, 42.4, 43.3, 55.9, 56.9, 57.0, 61.6, 72.0, 125.9, 128.4, 128.5, 141.8, 171.6, 171.8, 218.9 |
| MS m/z | 391 (M$^+$), 373 (M$^+$ – H$_2$O), 175 (base peak) |
| HRMS | for C$_{22}$H$_{36}$O$_6$ cal'd [C, 67.67; H, 7.74] measured [C, 67.41; H, 7.70] |
| [α]$_p^{24}$ | +18.34° (c 0.66, CHCl$_3$) |
| Optical purity (HPLC analysis)- | 91% e.e. HPLC analysis conditions: CHIRALPAK AS manufactured by Daicel Chemical Industries Co., Ltd., isopropanol/hexane = 1/9, detection: 254 nm, flow rate: 1.0 ml/min. |

EXAMPLE 14

Three-component Combination-type Reaction

Cyclopentenone (84 mg, 1.0 mmol), diethyl methylmalonate (138 mg, 1.0 mmol), and benzaldehyde (122 mg, 1.2 mmol) were added to the solution of Al—Li-(R)-binaphthol complex obtained in Example 1 (0.1 M, 1.0 ml). The stirring was continued at room temperature for 72 hours to carry out the reaction below.

Chemical formula 24

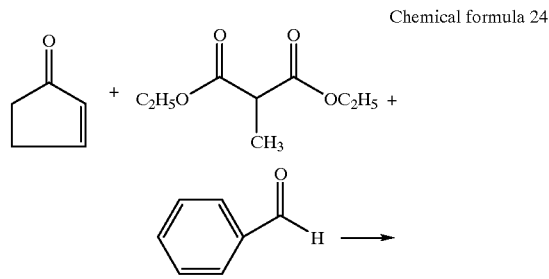

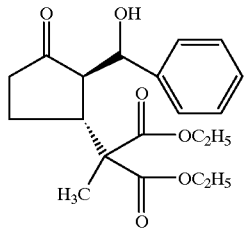

Then, the workup was performed as in Example 13 to obtain the three component combination compound of a final product in a yield of 82%. In order to analyze this reaction product in the same manner as in Example 6, the product was oxidized with pyridinium chlorochromate (hereinafter abbreviated as PCC) to obtain the diketone compound as shown in chemical formula 25. The results of the analysis of this diketone compound are shown in Table 11. According to the HPLC analysis results shown in this Table, the optical purity of the diketone compound was 89% e.e. Therefore, it is considered that the optical purity of the three-component combination-type reaction product in this Example is also 89% e.e.

Chemical formula 25

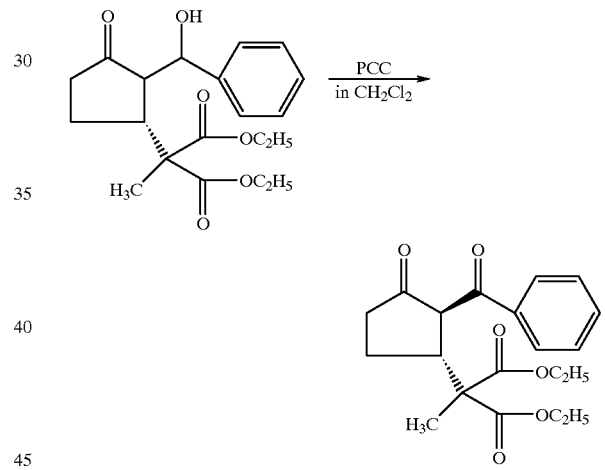

TABLE 11

| | |
|---|---|
| IR (neat) | 3468 cm$^1$, 1728 cm$^{-1}$, 11677 cm$^{-1}$, 1260 cm$^{-1}$ |
| $^1$H NMR (CDCl$_3$) (δ) | 1.04(t, J=7.3Hz, 3H), 1.21 (t, J=7.3Hz, 3H), 1.49(s, 3H), 1.03–2.03(m, 1H), 2.26–2.48(m, 3H), 3.55–3.68(m, 1H), 3.87 (dq, J=7.3, 10.9Hz, 1H), 4.03(dq, J=7.3, 10.9Hz, 1H), 4.13 (q, J=7.3Hz, 2H), 4.77 (d, J=8.6Hz, 1H), 7.45–7.52(m, 2H), 7a.55–6.62 (m, 1H), 8.00–8.05 (m, 1H) |
| $^{13}$C NMR (CDCl$_3$) (δ) | 13.6, 13.9, 19.7, 22.7, 38.9, 44.4, 55.6, 59.4, 61.4, 128.5, 129.4, 133.3, 136.5, 171.1, 195.1, 211.0 |
| MS m/z | 361 (M$^+$), 360 (M$^+$ – H$_2$O), 105 (base peak) |
| HRMS | for C$_{20}$H$_{24}$O$_6$ cal'd [C, 66.65; H, 6.71] measured [C, 66.38; H, 6.65] |

TABLE 11-continued

| | |
|---|---|
| $[\alpha]_D^{24}$ | −22.00° (c 1.02, $CHCl_3$) |
| Optical purity (HPLC analysis) | 89% e.e. A diketone compound which had been oxidized with pyridinium chlorochromate in methylene chloride was subject to HPLC analysis. HPLC analysis conditions: CHIRALCEL OJ manufactured by Daicel Chemical Industries Co., Ltd., isopropanol/hexane = 1/4, detection: 254 nm, flow rate: 0.5 ml/min. |

EXAMPLE 15

Asymmetric Hydrophosphonylation Reaction

The solution of the Al—Li-(R)-binaphthol complex (hereinafter abbreviated as ALB) obtained in Example 1 in tetrahydrofuran (0.1 M, 0.36 ml) was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring for 30 minutes, the reaction vessel was cooled to −40° C. After it was maintained at this temperature for 15 minutes, benzaldehyde (0.48 mmol) was added thereto. After reacting for 90 hours, 1N hydrochloric acid was added thereto to stop the reaction. The mixture was extracted with ethyl acetate (10 ml×three times), and the combined extracts were washed with brine and dried over $Na_2SO_4$. The solvent was distilled, and the residue was purified by flash column chromatography (acetone/hexane=1/5, on $SiO_2$) to obtain dimethyl (S)-hydroxyphenylmethylphosphonate as a final product in a yield of 95%. The chemical reaction in this Example is shown in chemical formula 26.

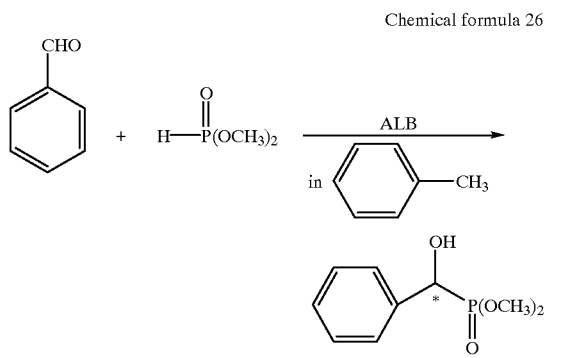

Chemical formula 26

The results of an analysis of this reaction product are shown in Table 12.

TABLE 12

| | |
|---|---|
| IR (neat) | 3261 $cm^{-1}$, 1235 $cm^{-1}$ |
| $^1H$ NMR ($CDCl_3$) (δ) | 3.30(dd, J=4.0, 5.3Hz, 1H), 3.61 (d, J=9.9Hz, 3H), 3.63 (d, J=9.9Hz, 3H), 4.98 (dd, J=5.0, 9.9Hz, 1H), 7.2–7.5 (m, 5H) |
| $^{13}C$ NMR ($CDCl_3$) (δ) | 53.6(J=7.3Hz), 53.9 (J=7.3Hz), 70.6(J=159.9Hz), 127.0(J=159.9Hz), 128.2 (J=3.7Hz), 128.4(J=2.5Hz), |

TABLE 12-continued

| | |
|---|---|
| | 136.3 |
| MS m/z | 216 ($M^+$) |
| HRMS | for $C_9H_{13}O_4P_1$ cal'd [C, 50.00; H, 6.06], measured [C, 49.80; H, 6.05] |
| Optical purity (HPLC analysis) | 90% e.e. HPLC analysis conditions: CHIRALPAK AS manufactured by Daicel Chemical Industries Co., Ltd., isopropanol/hexane = 1/4, detection: 254 nm, flow rate: 0.9 ml/min. |

EXAMPLE 16

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring for 30 minutes, the reaction vessel was cooled to −40° C., and it was maintained at this temperature for 15 minutes. Benzaldehyde (0.40 mmol) then was added thereto. After reacting for 51 hours, 1N hydrochloric acid was added thereto to stop the reaction. The mixture -was extracted with ethyl acetate (10 ml×three times). The combined extracts were washed with brine and dried over $Na_2SO_4$. The solvent was distilled, and the residue was purified by flash column chromatography (acetone/hexane=1/5, on $SiO_2$) to obtain dimethyl (S)-hydroxy-phenylmethylphosphonate as final product in a yield of 90%. The chemical reaction in this Example is shown in chemical formula 27.

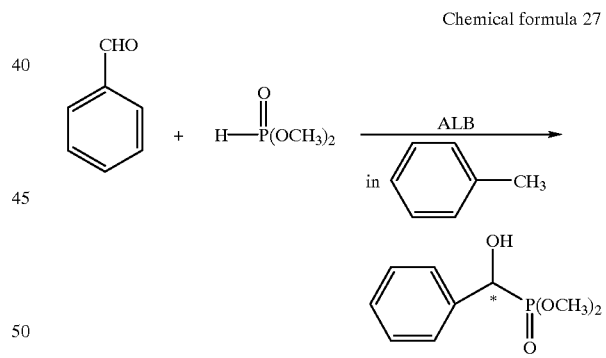

Chemical formula 27

The results of an analysis of this reaction product are shown in Table 13.

TABLE 13

| | |
|---|---|
| IR (KBr) | 3261 $cm^{-1}$, 1235 $cm^{-1}$ |
| $^1H$ NMR ($CDCl_3$) (δ) | 3.30(dd, J=4.0, 5.3Hz, 1H), 3.61 (d, J=9.9Hz, 3H), 3.63 (d, J=9.9Hz, 3H), 4.98 (dd, J=5.0, 9.9Hz, 1H), 7.2–7.5 (m, 5H) |
| $^{13}C$ NMR($CDCl_3$) (δ) | 53.6(J=7.3Hz), 53.9 (J=7.3Hz), 70.6(J=159.9Hz), 127.0(J=159.9Hz), 128.2 (J=3.7Hz), 128.4(J=2.5Hz), 136.2 |

TABLE 13-continued

| | |
|---|---|
| MS m/z | 216 (M+) |
| HRMS | for $C_9H_{13}O_4P_1$<br>cal'd [C, 50.00; H, 6.06],<br>measured [C, 49.80; H, 6.05] |
| $[\alpha]_p^{24}$ | −44.3° (c 1.0, $CHCl_3$) |
| Optical purity<br>(HPLC analysis) | 85% e.e. HPLC analysis conditions: CHIRALPAK AS manufactured by Daicel Chemical Industries Co., Ltd., isopropanol/hexane = 1/4, detection: 254 nm, flow rate: 0.9 ml/min. |

EXAMPLES 17–20

Asymmetric Hydrophosphonylation Reaction

Further, the same reactions were carried out as in chemical formula 27 by changing the reaction solvents to obtain analysis results shown in Table 14.

TABLE 14

| Example No. | Solvent | Reaction time (hr) | Yield (%) | Optical purity (%) |
|---|---|---|---|---|
| 17 | Tetrahydrofuran | 36.5 | 61 | 73 |
| 18 | Toluene | 36.5 | 88 | 83 |
| 19 | Methylene chloride | 36.5 | 49 | 80 |
| 20 | Ethyl ether | 36.5 | 58 | 78 |

EXAMPLE 21

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 µl, 0.40 mmol) at room temperature. After stirring for 30 minutes, the reaction vessel was cooled to −40° C., and it was maintained at this temperature for 15 minutes. Then p-chlorobenzaldehyde (0.40 mmol) was added thereto. After reacting for 38 hours, 1N hydrochloric acid was added thereto to stop the reaction. The mixture was extracted with ethyl acetate (10 ml×three times), and the combined extracts were washed with brine and dried over $Na_2SO_4$. The solvent was distilled, and the residue was purified by flash column chromatography (acetone/hexane=1/5, on $SiO_2$) to obtain dimethyl (S)-hydroxy(p-chlorophenyl)methylphosphonate as a final product in a yield of 90%. The chemical reaction in this Example is shown in chemical formula 28.

Chemical formula 28

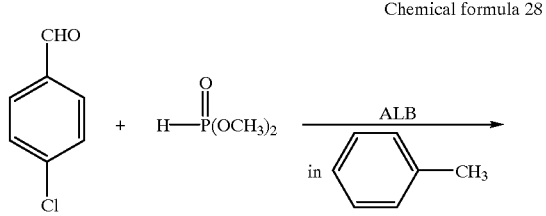

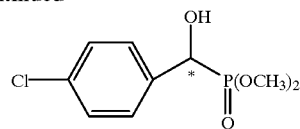

The results of the analysis of this reaction product are shown in Table 15.

TABLE 15

| | |
|---|---|
| IR (KBr) | 3257 $cm^{-1}$, 1233 $cm^{-1}$ |
| $^1H$ NMR ($CDCl_3$)<br>(δ) | 2.95(dd, J=4.6, 10.6Hz, 1H), 3.62<br>(d, J=10.6Hz, 3H), 3.64<br>(d, J=10.6Hz, 3H), 5.05<br>(dd, J=5.0, 10.9Hz, 1H), 7.35<br>(d, J=8.5Hz, 2H), 7.43<br>(dd, J=3.0, 8.5Hz, 2H) |
| $^{13}C$ NMR($CDCl_3$)<br>(δ) | 53.6(J=7.4Hz), 54.1(J=7.4Hz),<br>70.0(J=159.9Hz), 128.4<br>(J=6.0Hz), 128.5(J=2.4Hz), 133.9<br>(J=3.7Hz), 135.1(J=2.4Hz) |
| MS m/z | 250 (M+) |
| HRMS | for $C_9H_{12}Cl_1O_4P_1$<br>cal'd [C, 43.13; H, 4.83],<br>measured [C, 42.88; H, 4.80] |
| $[\alpha]_p^{24}$ | −49.1° (c 1.0, $CHCl_3$) |
| Optical purity<br>(HPLC analysis) | 83% e.e. HPLC analysis conditions: CHIRALPAK AS manufactured by Daicel Chemical Industries Co., Ltd., isopropanol/hexane = 1/4, detection: 254 nm, flow rate: 0.5 ml/min. |

EXAMPLE 22

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 µl, 0.40 mmol) at room temperature. After stirring at room temperature for 30 minutes, the reaction vessel was cooled to −40° C., and it was maintained at this temperature for 0.15 minutes. Then p-methylbenzaldehyde (0.40 mmol) was added thereto. After reacting for 92 hours, 1N hydrochloric acid was added thereto to stop the reaction. The mixture was extracted with ethyl acetate (10 ml×three times), and the combined extracts were washed with brine and dried over $Na_2SO_4$. The solvent was distilled, and the residue was purified by flash column chromatography (acetone/hexane= 1/5, on $SiO_2$) to obtain dimethyl (S)-hydroxy(p-methylphenyl)methylphosphonate as a final product in a yield of 82%. The chemical reaction in this Example is shown in chemical formula 29.

Chemical formula 29

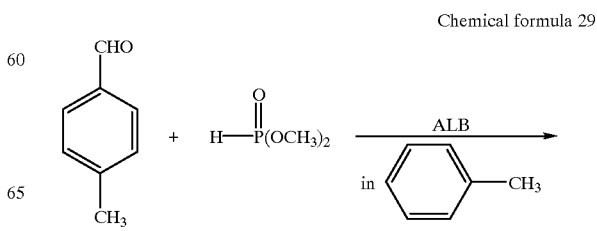

21

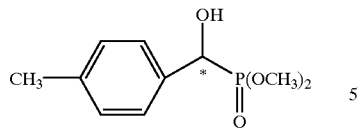

The results of the analysis of this reaction product are shown in Table 16.

TABLE 16

| | |
|---|---|
| IR (KBr) | 3250 cm$^{-1}$, 1256 cm$^{-1}$ |
| $^1$H NMR(CDCl$_3$) ($\delta$) | 2.28(d,J=1.6, 3H), 2.80 (bs, 1H), 3.63(d,J=10.8Hz, 3H), 3.65(d,J=10.8Hz, 3H), 4.93 (d, J=10.6Hz, 1H), 7.12 (d, J=7.9Hz, 2H), 7.30 (dd, J=2.0, 7.9Hz, 2H) |
| $^{13}$C NMR (CDCl$_3$) ($\delta$) | 21.2, 53.6(J=7.3Hz), 53.9 (J=7.3Hz), 70.5(J=159.9Hz), 126.9(J=6.1Hz), 129.1 (J=2.4Hz), 133.3, 138.0 (J=2.4Hz) |
| MS m/z | 230 (M$^+$) |
| HRMS | for C$_{10}$H$_{15}$O$_4$P$_1$ cal'd [C, 52.18; H, 6.57] measured [C, 52.17; H, 6.45] |
| $[\alpha]_p^{24}$ | −49.5° (c 1.0, CHCl$_3$) |
| Optical purity (HPLC analysis) | 86% e.e. HPLC analysis conditions: CHIRALPAK AS manufactured by Daicel Chemical Industries Co., Ltd., isopropanol/hexane = 1/4, detection: 254 nm, flow rate: 0.5 ml/min. |

EXAMPLE 23

Asymmetric Hydrophosphonylation Reaction

The solution of ALE in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring for 30 minutes at room temperature, the reaction vessel was cooled to −40° C., and it was maintained at this temperature for 15 minutes. Then, p-methoxybenzaldehyde (0.40 mmol) was added thereto. After reacting for 115 hours, 1N hydrochloric acid was added thereto to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane= 1/5, on SiO$_2$) to obtain dimethyl (S)-hydroxy(p-methoxyphenyl)methylphosphonate as a final product in a yield of 88%. The chemical reaction in this Example is shown in chemical formula 30.

Chemical formula 30

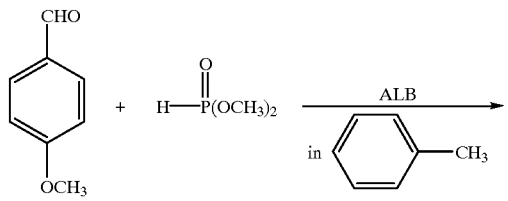

22

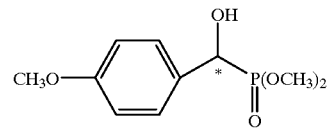

The results of the analysis of this reaction product are shown in Table 17.

TABLE 17

| | |
|---|---|
| IR (KBr) | 3338 cm$^{-1}$, 1236 cm$^{-1}$ |
| $^1$H NMR (CDCl$_3$) ($\delta$) | 3.19(bs, 1H), 3.63 (d, J=10.4Hz, 3H), 3.65 (d, J=10.4Hz, 3H), 3.74(s, 3H), 4.91 (d, J=9.9Hz, 1H), 6.85 (d, J=8.3Hz, 2H), 7.34(dd, J=2.0, 8.3Hz, 2H) |
| $^{13}$C NMR (CDCl$_3$) ($\delta$) | 53.5(J=7.3Hz), 53.8(J=7.3Hz), 55.2, 70.0(J=162.4Hz), 113.8, 128.4, 159.5(J=2.5Hz) |
| MS m/z | 246 (M$^+$) |
| HRMS | for C$_{10}$H$_{15}$O$_5$P$_1$ cal'd [C, 48.79; H, 6.19] measured [C, 48.81; H, 6.07] |
| $[\alpha]_p^{24}$ | −38.7° (c 1.0, CHCl$_3$) |
| Optical purity (HPLC analysis) | 78% e.e. HPLC analysis conditions: CHIRALPAK AS manufactured by Daicel Chemical Industries Co., Ltd., isopropanol/hexane = 1/4, detection: 254 nm, flow rate: 1.0 ml/min. |

EXAMPLE 24

Asymmetric Hydrophosphonylation Reaction

Dimethyl phosphite (37 μl, 0.40 mmol) was added to the solution of ALB in tetrahydrofuran (0.1 M, 0.40 ml) obtained in Example 1 at room temperature. After stirring at room temperature for 30 minutes, the reaction vessel was cooled to −78° C., and it was maintained at this temperature for 15 minutes. Then p-nitrobenzaldehyde (0.40 mmol) was added thereto. After the temperature was raised to room temperature, the stirring was continued for 12 hours. Hydrochloric acid (1N) was added thereto to stop the reaction, and the mixture was extracted with ethyl acetate (10 ml×three times). The combined extracts were washed with brine and dried over Na$_2$SO$_4$. The solvent was distilled, and the residue was purified by flash column chromatography (acetone/hexane=1/5, on SiO$_2$) to obtain dimethyl (S)-hydroxy(p-nitrophenyl)methylphosphonate as a final product in a yield of 81%. The chemical reaction in this Example is shown in chemical formula 31.

Chemical formula 31

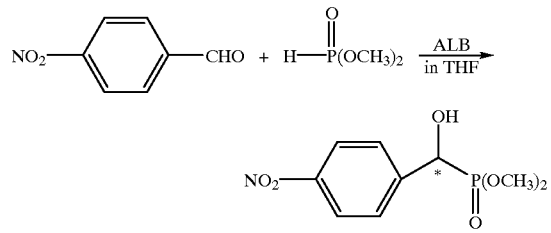

The results of the analysis of this reaction product are shown in Table 18.

TABLE 18

| $^1$H NMR (CDCl$_3$) (δ) | 3.85(d, J=10.9Hz, 3H), 3.87 (d, J=10.9Hz, 3H), 5.30 (d, J=11.6Hz, 1H), 7.77 (dd, J=2.0, 8.0Hz, 2H), 8.34 (d, J=8.0Hz, 2H) |
|---|---|
| Optical purity (HPLC analysis) | 23% e.e. HPLC analysis conditions: CHIRALPAK AS manufactured by Daicel Chemical Industries Co., Ltd., isopropanol/hexane = 1/9, detection: 254 nm, flow rate: 1.0 ml/min. |

EXAMPLE 25

Asymmetric Hydrophosphonylation Reaction

Dimethyl phosphite (37 μl, 0.40 mmol) was added to the solution of ALB in tetrahydrofuran (0.1 M, 0.40 ml) obtained in Example 1 at room temperature. After stirring at room temperature for 30 minutes, the reaction vessel was cooled to −40° C., and it was maintained at this temperature for 15 minutes. p-Dimethylaminobenzaldehyde (0.40 mmol) was added thereto. After reacting for 48 hours, 1N hydrochloric acid was added thereto to stop the reaction. The mixture was extracted with ethyl acetate (10 ml×three times), and the combined mixture were washed with brine and dried over Na$_2$SO$_4$. The solvent was distilled, and the residue was purified by flash column chromatography (acetone/hexane=1/5, on SiO$_2$) to obtain dimethyl (S)-hydroxy (p-dimethylaminophenyl)-methylphosphonate as a final product in a yield of 71%. The chemical reaction in this Example is shown in chemical formula 32.

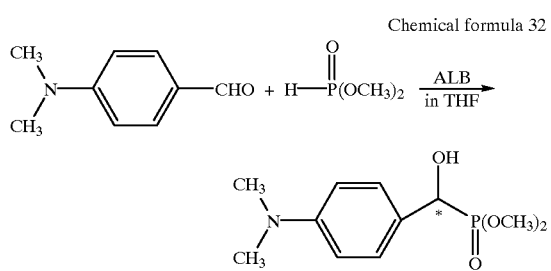

Chemical formula 32

TABLE 19

| $^1$H NMR (CDCl$_3$) (δ) | 2.96(s, 6H), 3.64(d, J=10.2Hz, 3H), 3.74(d, J=10.6Hz, 3H), 4.92 (dd, J=5.0, 9.9Hz, 1H), 6.72 (d, J=8.9Hz, 2H), 7.35 (dd, J=2.0, 8.9Hz, 2H) |
|---|---|
| Optical purity (HPLC analysis) | 15% e.e. HPLC analysis conditions: CHIRALPAK AS manufactured by Daicel Chemical Industries Co., Ltd., isopropanol/hexane = 1/2, detection: 254 nm, flow rate: 1.0 ml/min. |

EXAMPLE 26

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added diethyl phosphite (0.40 mmol) at room temperature. After stirring at room temperature for 30 minutes, the reaction vessel was cooled to −40° C., and it was maintained at this temperature for 15 minutes. Then, benzaldehyde (0.40 mmol) was added thereto. After reacting for 90 hours, 1N hydrochloric acid was added thereto to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane=1/5, on SiO$_2$) to obtain diethyl (S)-hydroxy-phenylmethylphosphonate as a final product in a yield of 39%. The chemical reaction in this Example is shown in chemical formula 33.

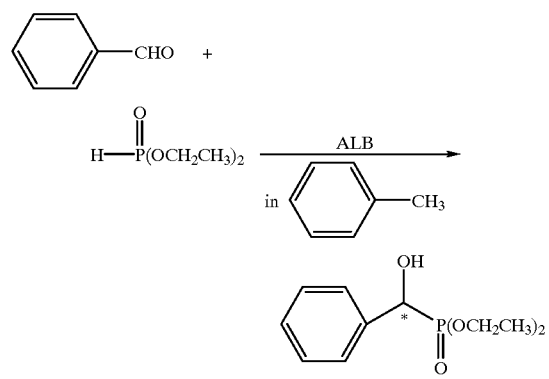

Chemical formula 33

TABLE 20

| Optical purity (HPLC analysis) | 73% e.e. HPLC analysis conditions: CHIRALPAK AS manufactured by Daicel Industries Co., Ltd., isopropanol/hexane = 1/4, detection: 254 nm, flow rate: 0.8 ml/min. |
|---|---|

EXAMPLE 27

Asymmetric Hydrophosphonylation Reaction

The same procedure as shown in Example 26 was used, except that dibutyl phosphite was used in place of the diethyl phosphite used in Example 26 to afford dibutyl (S)-hydroxy-phenylmethylphosphonate as a final product in a yield of 42%.

The analysis results of this reaction product are shown in Table 21.

TABLE 21

| Optical purity (HPLC analysis) | 67% e.e. HPLC analysis conditions: CHIRALPAK AS manufactured by Daicel Industries Co., Ltd., isopropanol/hexane = 1/9, detection: 254 nm, flow rate: 1.0 ml/min. |
|---|---|

EXAMPLE 28

Asymmetric Hydrophosphonylation Reaction

The same manner as shown in Example 26 was adopted except that dibenzyl phosphite was used in place of diethyl phosphite used in Example 26 and that the reaction was performed at room temperature for 6.5 hours to afford dibenzyl (S)-hydroxy-phenylmethylphosphonate of a final product in a yield of 60%. The analysis results on this reaction product are shown in Table 22.

TABLE 22

| Optical purity (HPLC analysis) | 8.4% e.e. HPLC analysis conditions: CHIRALPAK AS manufactured by Daicel Industries Co., Ltd., isopropanol/hexane = 1/9, detection: 254 nm, flow rate: 1.0 ml/min. |
|---|---|

EXAMPLE 29

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring at room temperature for 30 minutes, the reaction vessel was cooled to −40° C., and it was maintained at this temperature for 15 minutes. Then, cinnamaldehyde (0.40 mmol) was added thereto. After reacting for 81 hours, 1N hydrochloric acid was added thereto to stop the reaction. The mixture was extracted with ethyl acetate (10 ml×three times), and the combined extracts were washed with brine and dried over $Na_2SO_4$. The solvent was distilled, and the residue was purified by flash column chromatography (acetone/hexane=1/5, on $SiO_2$) to obtain dimethyl (S,E)-1-hydroxy-3-phenyl-2-propenylphosphonate as a final product in a yield of 85%. The chemical reaction in this Example is shown in chemical formula 34.

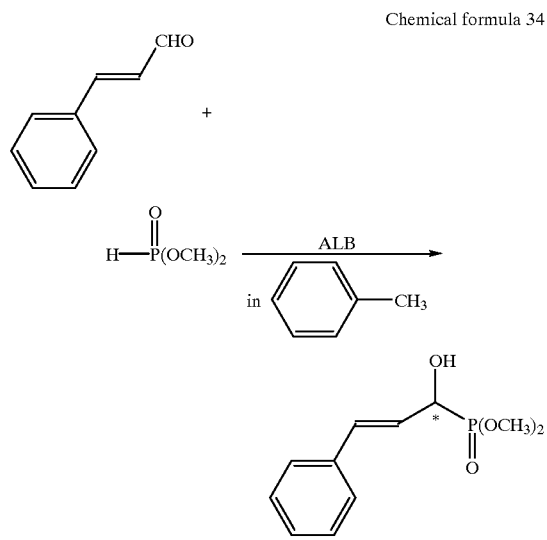

Chemical formula 34

The results of the analysis of this reaction product are shown in Table 23.

TABLE 23

| IR (KBr) | 3258 cm$^{-1}$, 1243 cm$^{-1}$ |
|---|---|
| $^1$H NMR (CDCl$_3$) | 3.77(d, J=10.3Hz, 3H), 3.78 |
| (δ) | (d, J=10.3Hz, 3H), 4.64 (ddd, J=1.7, 6.3, 12.9Hz, 1H), 6.26 (dt, J=5.6, 15.8Hz, 1H), 6.73 (dd, J=5.0, 15.8Hz, 1H), 7.30(m, 5H) |
| $^{13}$C NMR (CDCl$_3$) (δ) | 53.7(J=7.3Hz), 53.9(J=7.3Hz), 69.3(J=2.5Hz) |
| MS m/z | 242 (M$^+$) |
| HRMS | for $C_{11}H_{15}O_4P_1$ cal'd [C, 54.55;H, 6.24], measured [C, 54.28;H, 5.96] |
| $[α]_p^{24}$ | −21.4° (c 1.0, CHCl$_3$) |
| Optical purity (HPLC analysis) | 82% e.e. HPLC analysis conditions: CHIRALPAK AS manufactured by Daicel Chemical Industries Co., Ltd., isopropanol/hexane = 1/4, detection: 254 nm, flow rate: 1.2 ml/min. |

EXAMPLE 30

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring at room temperature for 30 minutes, the reaction vessel was cooled to −40° C., and it was maintained at this temperature for 15 minutes, then (E)-β-methylcinnamaldehyde (0.40 mmol) was added thereto. After reacting for 81 hours, 1N hydrochloric acid was added thereto to stop the reaction. The mixture was extracted with ethyl acetate (10 ml×three times), and the combined extracts were washed with brine and dried over $Na_2SO_4$. The solvent was distilled, and the residue was purified by flash column chromatography (acetone/hexane= 1/5, on $SiO_2$) to obtain dimethyl (S,E)-1-hydroxy-3-methyl-3-phenyl-2-propenylphosphonate as a final product in a yield of 93%. The chemical reaction in this Example is shown in chemical formula 35.

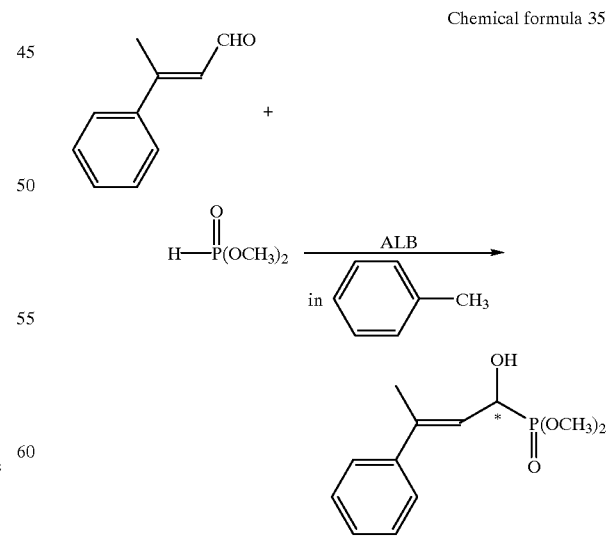

Chemical formula 35

The results of the analysis of this reaction product are shown in Table 24.

TABLE 24

| | |
|---|---|
| IR (KBr) | 3245 cm$^{-1}$, 1031 cm$^{-1}$ |
| $^1$H NMR (CDCl$_3$) (δ) | 2.14(dd, J=1.0, 3.3Hz, 3H), 3.10 (bs, 1H), 3.82(d, J=10.6Hz, 3H), 3.84(d, J=10.6Hz, 3H), 4.89 (t, J=9.2, 10.6Hz, 1H), 5.87 (dt, J=7.2, 15.5Hz, 1H), 7.36(m, 5H) |
| $^{13}$C NMR (CDCl$_3$) (δ) | 16.8, 53.6(J=7.4Hz), 53.8 (J=7.3Hz), 66.3(J=163.5Hz), 122.0 (J=3.7Hz), 126.0, 127.7, 128.3, 140.9(J=13.5Hz), 142.4 |
| MS m/z | 256 (M$^+$) |
| HRMS | for C$_{12}$H$_{17}$O$_4$P$_1$ cal'd [C, 56.25; h, 6.69], measured [C, 54.02; H, 6.91] |
| $[\alpha]_p^{24}$ | −12.8° (c 1.0, CHCl$_3$) |
| Optical purity (HPLC analysis) | 89% e.e. HPLC analysis conditions: CHIRALPAK AS manufactured by Daicel Chemical Industries Co., Ltd., isopropanol/hexane = 5/95, detection: 254 nm, flow rate: 1.0 ml/min. |

EXAMPLE 31

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring at room temperature for 30 minutes, the reaction vessel was cooled to −40° C., and it was maintained at this temperature for 15 minutes. Then 3-methyl-2-butenal (0.40 mmol) was added thereto. After reacting for 81 hours, 1N hydrochloric acid was added thereto to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane=1/5, on SiO$_2$) to obtain dimethyl (S)-1-hydroxy-3-methyl-2-butenylphosphonate as a final product in a yield of 72%. The chemical reaction in this Example is shown in chemical formula 36.

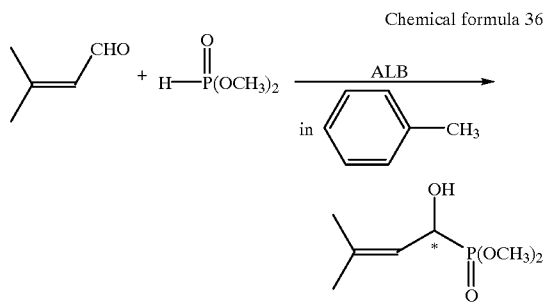

Chemical formula 36

The results of the analysis of this reaction product are shown in Table 25.

TABLE 25

| | |
|---|---|
| IR (KBr) | 3274 cm$^{-1}$, 1052 cm$^{-1}$ |
| $^1$H NMR (CDCl$_3$) (δ) | 1.71(dd, J=1.3, 3.0Hz, 3H), 1.81 (dd, J=1.0, 4.0Hz, 3H), 3.18(bs, 1H), 3.80(d, J=10.5Hz, 3H), 3.82 (d, J=10.5Hz, 3H), 4.66 (dt, 5.5, 9.1, 9.2, 1H), 5.33(m, 1H) |
| $^{13}$C NMR (CDCl$_3$) (δ) | 18.5, 25.9, 53.4(J=6.1Hz), 53.5 (J=7.4Hz), 65.5(J=163.6Hz), 119.4 (J=2.4Hz), 139.6(J=14.6Hz) |
| MS m/z | 191 (M$^+$) |
| HRMS | for C$_7$H$_{15}$O$_4$P$_1$ cal'd [C, 43.30; H, 7.79], measured [C, 43.01; H, 7.80] |
| $[\alpha]_p^{24}$ | −54.4° (c 0.65, CHCl$_3$) |
| Optical purity (HPLC analysis) | 68% e.e. HPLC analysis conditions: CHIRALPAK AS manufactured by Daicel Chemical Industries Co., Ltd., isopropanol/hexane = 1/4, detection: differential refraction |

EXAMPLE 32

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring at room temperature for 30 minutes, the reaction vessel was cooled to −40° C., and it was maintained at this temperature for 15 minutes. Then 2-hexenylaldehyde (0.40 mmol) was added thereto. After reacting for 39 hours, 1N hydrochloric acid was added thereto to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane=1/5, on SiO$_2$) to obtain dimethyl (E,S)-1-hydroxy-2-hexenylphosphonate as a final product in a yield of 53%. The chemical reaction in this Example is shown in chemical formula 37.

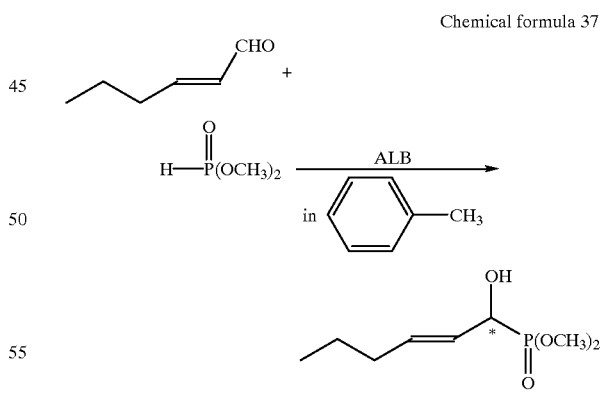

Chemical formula 37

The results of the analysis of this reaction product are shown in Table 26.

TABLE 26

| | |
|---|---|
| IR (KBr) | 3299 cm$^{-1}$, 1237 cm$^{-1}$ |
| $^1$H NMR (CDCl$_3$) (δ) | 0.91(d, J=7.3Hz, 3H), 1.43 (dt, J=7.3, 7.6Hz, 2H), 2.07(m, 2H), 3.79(d, J=10.2Hz, 3H), 3.81 |

TABLE 26-continued

| | |
|---|---|
| | (d, J=10.2Hz, 3H), 4.46 (dd, J=7.3, 10.6Hz, 1H), 5.60(m, 1H), 5.90(m, 1H) |
| $^{13}$C NMR (CDCl$_3$) (δ) | 13.6, 22.0, 34.4, 53.5(J=7.3Hz), 53.7(J=7.3Hz), 69.2(J=162.3Hz), 124.2(J=3.6Hz), 135.4(J=12.2Hz) |
| MS m/z | 208 (M$^+$) |
| $[\alpha]_p^{24}$ | −9.7° (c 0.95, CHCl$_3$) |
| Optical purity (HPLC analysis) | 55% e.e. HPLC analysis conditions: CHIRALPAK AS manufactured by Daicel Chemical Industries Co., Ltd., iso-propanol/hexane = 1/4, flow rate: 1.0 ml/min., detection: differential refraction |

EXAMPLE 33

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring at room temperature for 30 minutes, the 20 reaction vessel was cooled to −40° C., and it was maintained at this temperature for 15 minutes. Then (E)-α-methylcinnamaldehyde (0.40 mmol) was added thereto. After reacting for 61 hours, 1N hydrochloric acid was added thereto to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane=1/5, on SiO$_2$) to obtain dimethyl-(E)-(S)-1-hydroxy-2-methyl-3-phenyl-2-propenyl phosphonate as a final product in a yield of 47%. The chemical reaction in this Example is shown in chemical formula 38.

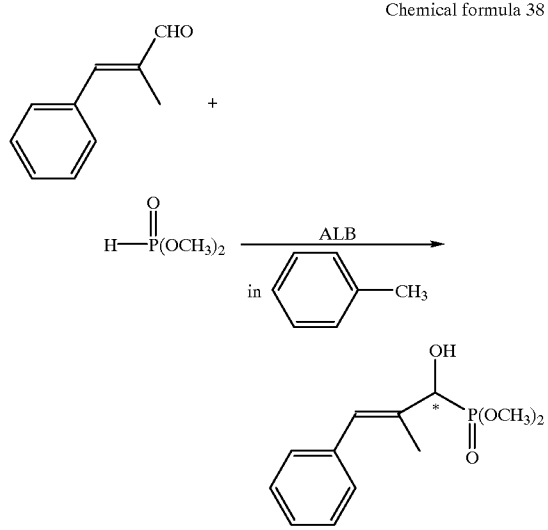

Chemical formula 38

The results of an analysis of this reaction product are shown in Table 27.

TABLE 27

| | |
|---|---|
| $^1$H NMR (CDCl$_3$) (δ) | 1.96(dd, J=1.3, 3.3Hz, 3H), 3.76 (d, J=10.8Hz, 3H), 3.78 (d, J=10.6Hz, 3H), 4.47 (dd, J=4.3, 12.5Hz, 1H), 6.63 (d, J=4.6Hz, 1H), 7.21(m, 5H) |
| Optical purity (HPLC analysis) | 56% e.e. HPLC analysis conditions: CHIRALPAK AS manufactured by Daicel Chemical Industries Co., Ltd., isopropanol/hexane = 1/4, detection: 254 nm, flow rate: 0.5 ml/min. |

EXAMPLE 34

Asymmetric Hydrophosphonylation Reaction

The same procedure as shown in Example 33 was used, except that 2-methylpropenal was used in place of the (E)-α-methylcinnamaldehyde (0.40 mmol) used in Example 33 and that the reaction was carried out for 35 hours to afford dimethyl (S,E)-1-hydroxy-2-methyl-2-propenylphosphonate as a final product in a yield of 65%. The chemical reaction in this Example is shown in chemical formula 39.

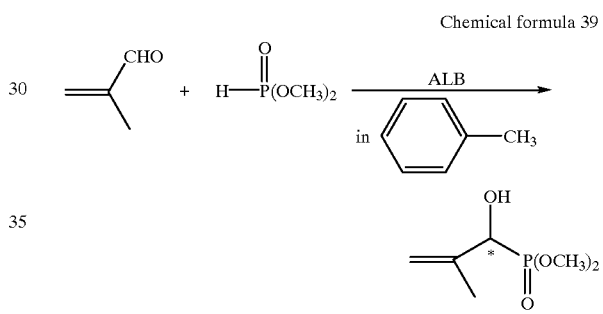

Chemical formula 39

The results of an analysis of this reaction product are shown in Table 28.

TABLE 28

| | |
|---|---|
| $^1$H NMR(CDCl$_3$) (δ) | 1.83(t, J=1.3, 1.0Hz, 3H)3.12 (dd, J=5.6, 10.2Hz, 1H), 3.75 (d, J=10.5Hz, 3H), 3.76 (d, J=10.5Hz, 3H), 4.38 (dd, J=5.0, 12.5Hz, 1H), 5.02 (t, J=1.3Hz, 1H), 5.13(d, J-4.6Hz, 1H) |
| Optical purity (HPLC analysis) | 56% e.e. HPLC analysis conditions: CHIRALPAK AS manufactured by Daicel Chemical Industries Co., Ltd., isopropanol/hexane = 1/4, detection: differential refraction, flow rate: 0.5 ml/min. |

EXAMPLE 35

Asymmetric Hydrophosphonylation Reaction

The same procedure as shown in Example 33 was used, except that cyclohexylidene-Δ$^1$α-acetaldehyde was used in place of the (E)-α-methylcinnamaldehyde (0.40 mmol) used in Example 33 and the reaction was carried out for 47 hours to afford dimethyl-(S)-cyclo-hexylidene-Δ$^1$α-1-hydroxyethylphosphonate in a yield of 65%. The chemical reaction in this Example is shown in chemical formula 40.

Chemical formula 40

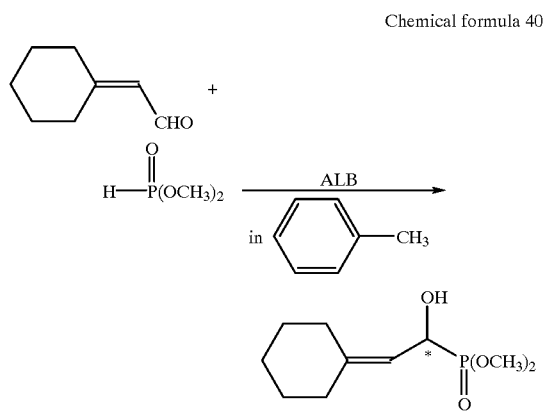

The results of an analysis of this reaction product are shown in Table 29.

TABLE 29

| $^1$H NMR (CDCl$_3$) ($\delta$) | 1.45(bs, 6H), 2.11(bs, 2H), 3.05 (bs, 1H), 3.74(d, J=10.6Hz, 3H), 3.75(d, J=10.6Hz, 3H), 4.70 (m, 1H), 5.21(m, 1H) |
|---|---|
| Optical purity (HPLC analysis) | 60% e.e. HPLC analysis conditions: CHIRALPAK AS manufactured by Daicel Chemical Industries Co., Ltd., isopropanol/ hexane = 1/4, detection: 254 nm, flow rate: 1.0 ml/min. |

EXAMPLE 36

Asymmetric Hydrophosphonylation Reaction

The solution of ALB in tetrahydrofuran (0.1 M, 0.40 ml) obtained in Example 1 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring at room temperature for 30 minutes, the reaction vessel was cooled to −40° C., and it was maintained at this temperature for 15 minutes. Then 2-methylpropionaldehyde (0.40 mmol) was added thereto. After reacting for 38 hours, 1N hydrochloric acid was added thereto to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane= 1/5, on SiO$_2$) to obtain dimethyl (S)-1-hydroxy-2-methylpropylphosphonate as a final product in a yield of 95%. The chemical reaction in this Example is shown in chemical formula 41.

Chemical formula 41

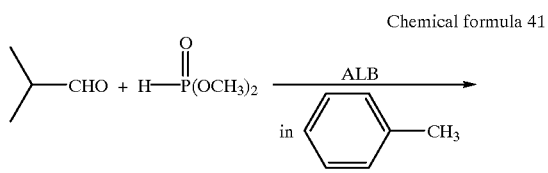

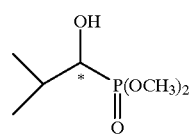

The results of an analysis of this reaction product are shown in Table 30.

TABLE 30

| $^1$H NMR (CDCl$_3$) ($\delta$) | 1.96(dd,J=1.3, 3.3Hz,3H), 3.76 (d,J=10.8Hz, 3H), 3.78 (d,J=10.6Hz, 3H), 4.47 (dd,J=4.3, 12.5Hz, 1H), 6.63 (d,J=4.6Hz, 1H), 7.21(m, 5H) |
|---|---|
| Optical purity (HPLC analysis) | 14% e.e. HPLC analysis conditions: CHIRALPAK AS manufactured by Daicel Chemical Industries Co., Ltd., isopropanol/hexane = 1/4, detection: differential refraction, flow rate: 0.5 ml/min. |

EXAMPLE 37

Asymmetric Hydrophosphonylation Reaction

The same procedure as shown in Example 36 was used, except that hexanal was used in place of the 2-methylpropionaldehyde used in Example 36 and the reaction was carried out for 20 hours to afford dimethyl (S)-1-hydroxyhexylphosphonate as a final compound in a yield of 90%. The chemical reaction in this Example is shown in chemical formula 42.

Chemical formula 42

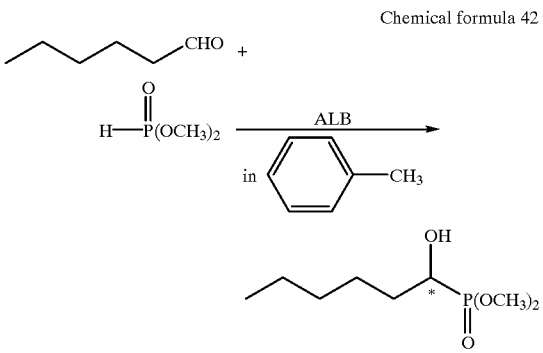

The results of an analysis of this reaction product are shown in Table 31.

TABLE 31

| $^1$H NMR (CDCl$_3$) ($\delta$) | 0.97(t, J=6.3, 3H), 1.40(m, 4H), 1.80(m, 4H), 3.87 (d, J=10.2Hz, 3H), 3.88 (d, J=10.2Hz, 3H), 3.92(m, 1H) |
|---|---|
| Optical purity (HPLC analysis) | 3% e.e. HPLC analysis conditions: CHIRALPAK AS manufactured by Daicel Chemical Industries Co., Ltd., isopropanol/hexane = 1/4, detection: 254 nm, flow rate: 0.5 ml/min. |

EXAMPLE 38

Asymmetric Hydrophosphonylation Reaction

The same procedure as shown in Example 36 was used, except that cyclohexanal was used in place of the 2-methylpropionaldehyde used in Example 36 and the reaction was carried out for 43 hours to afford dimethyl (S)-1-hydroxyhexyl phosphonate in a yield of 91%. The chemical reaction in this Example is shown in chemical formula 43.

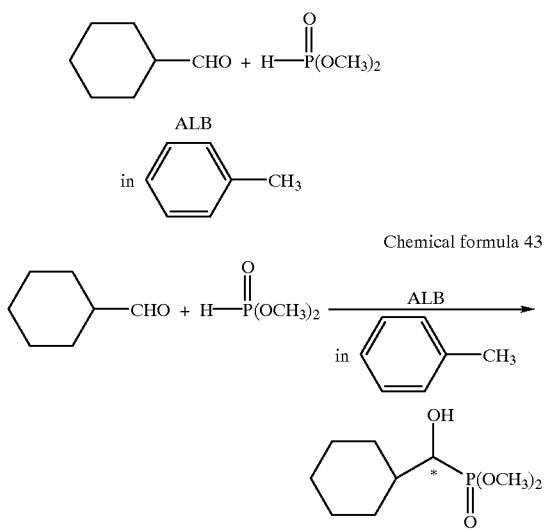

Chemical formula 43

The results of an analysis of this reaction product are shown in Table 32.

TABLE 32

| $^1$H NMR (CDCl$_3$) (δ) | 1.20(m, 6H), 1.78(m, 4H), 1.98 (d, J=11.9Hz, 1H), 2.52 (t, J=6.9Hz, 1H), 3.71 (q, J=6.9, 12.5Hz, 2H), 3.80 (d, J=10.6Hz, 3H), 3.82 (d, J=10.6Hz, 3H) |
|---|---|
| Optical purity HPLC analysis) | 24% e.e. HPLC analysis conditions: CHIRALPAK AS manufactured by Daicel Chemical Industries Co., Ltd., isopranol/hexane = 1/4, detection: differential refraction, flow rate: 0.5 ml/min. |

EXAMPLE 39

Asymmetric Hydrophosphonylation Reaction using Al—Li-(R)-6,6'-dibromobinaphthol (hereinafter abbreviated as ALB-Br)

The solution of ALB-Br in tetrahydrofuran (0.1M, 0.40 ml) obtained in Example 4 was concentrated at room temperature for 1 hour under reduced pressure, then 0.4 ml of toluene was added under an argon atmosphere. To this solution was added dimethyl phosphite (37 μl, 0.40 mmol). After stirring at room temperature for 30 minutes, the reaction vessel was cooled to −40° C., and it was maintained at this temperature for 15 minutes. Then benzaldehyde (0.40 mmol) was added thereto. After reacting for 59 hours, 1N hydrochloric acid was added to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane=1/5, on SiO$_2$) to obtain dimethyl (S)-hydroxy-phenylmethyl phosphonate as a final product in a yield of 91%. The chemical reaction in this Example is shown in chemical formula 44.

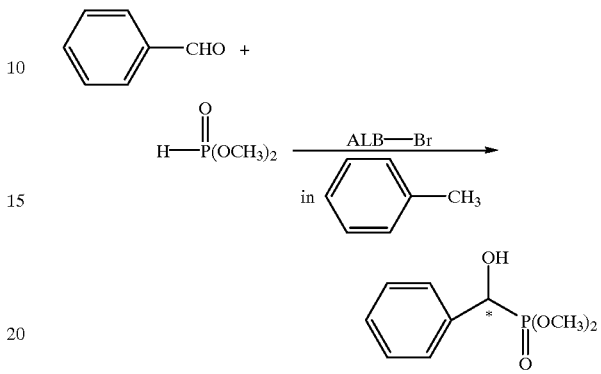

Chemical formula 44

The results of an analysis of this reaction product are shown in Table 33.

TABLE 33

| $^1$H NMR (CDCl$_3$) (δ) | 3.30(dd, J=4.0, 5.3Hz, 1H), 3.61 (d, J=9.9Hz, 3H), 3.63 (d, J=9.9Hz, 3H), 4.98 (dd, J=5.0, 9.9Hz, 1H), 7.2–7.5 (m, 5H) |
|---|---|
| Optical purity (HPLC analysis) | 68% e.e. HPLC analysis conditions: CHIRALPAK AS manufactured by Daicel Chemical Industries Co., Ltd., isopropanol/hexane = 1/4, detection: 254 nm, flow rate: 0.5 ml/min. |

EXAMPLE 40

Asymmetric Hydrophosphonylation Reaction using ALB-Br

The same procedure as shown in Example 39 was used, except that p-methoxybenzaldehyde was used in place of the benzaldehyde used in Example 39 to afford dimethyl (S)-hydroxy(p-methoxyphenyl)methylphosphate as a final product in a yield of 72%. The chemical reaction in this Example is shown in chemical formula 45.

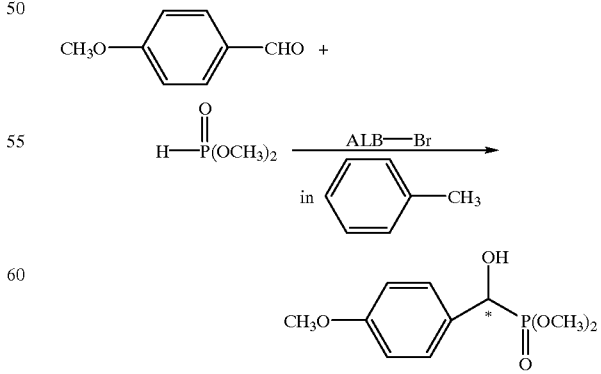

Chemical formula 45

The results of an analysis of this reaction product are shown in Table 34.

TABLE 34

| $^1$H NMR (CDCl$_3$) (δ) | 3.19(bs, 1H), 3.63(d, J=10.4Hz, 3H), 3.65(d, J=10.4Hz, 3H), 3.74(s, 3H), 4.91(d, J=9.9Hz, 1H), 6.85 (d, J=8.3Hz, 2H), 7.34 (dd, J=2.0, 8.3Hz, 2H) |
|---|---|
| Optical purity (HPLC analysis) | 35% e.e. HPLC analysis conditions: CHIRALPAK AS manufactured by Daicel Chemical Industries Co., Ltd., isopropanol/hexane = 1/4, detection: 254 nm, flow rate: 1.1 ml/min. |

EXAMPLE 41

Asymmetric Hydrophosphonylation Reaction using Al—Li-(R)-6,6'-dicyanobinaphthol (hereinafter abbreviated as ALB-CN)

The solution of ALB-CN in tetrahydrofuran (0.1M, 0.40 ml) obtained in Example 5 was concentrated at room temperature for 1 hour under reduced pressure, then 0.4 ml of toluene was added thereto under an argon atmosphere. To this solution was added dimethyl phosphite (37 μl, 0.40 mmol) at room temperature. After stirring at room temperature for 30 minutes, the reaction vessel was cooled to −40° C., and it was maintained at this temperature for 15 minutes. Then p-methoxybenzaldehyde (0.40 mmol) was added thereto. After reacting for 59 hours, 1N hydrochloric acid was added to stop the reaction. The mixture was extracted with ethyl acetate (10 ml×three times), and the combined extracts were washed with brine and dried over Na$_2$SO$_4$. The solvent was distilled, and the residue was purified by flash column chromatography (acetone/hexane=1/5, on SiO$_2$) to obtain dimethyl (R)-hydroxy(p-methoxyphenyl) methylphosphonate as a final product in a yield of 25%. The chemical reaction in this Example is shown in chemical formula 46.

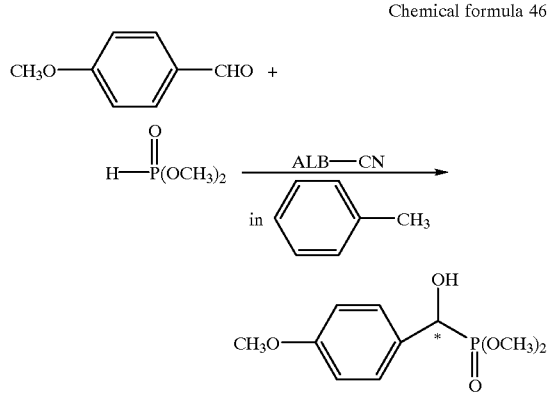

Chemical formula 46

The results of an analysis of this reaction product are shown in Table 35.

TABLE 35

| $^1$H NMR (CDCl$_3$) (δ) | 3.19(bs, 1H), 3.63(d, J=10.4Hz, 3H), 3.65(d, J=10.4Hz, 3H), 3.74(s, 3H), 4.91(d, J=9.9Hz, 1H), 6.85 (d, J=8.3Hz, 2H), 7.34 (dd, J=2.0, 8.3Hz, 2H) |
|---|---|
| Optical purity (HPLC analysis) | 35% e.e. HPLC analysis conditions: CHIRALPAK AS manufactured by Daicel Chemical Industries Co., Ltd., isopropanol/hexane = 1/4, detection: 254 nm, flow rate: 1.1 ml/min. |

EXAMPLE 42

Asymmetric Hydrophosphonylation Reaction using ALB-CN

The same procedure as shown in Example 41 was used, except that 2-methylpropionaldehyde was used in place of the p-methoxybenzaldehyde used in Example 41 to afford dimethyl (S)-1-hydroxy-2-methylpropylphosphonate as a final product in a yield of 66%. The chemical reaction in this Example is shown in chemical formula 47.

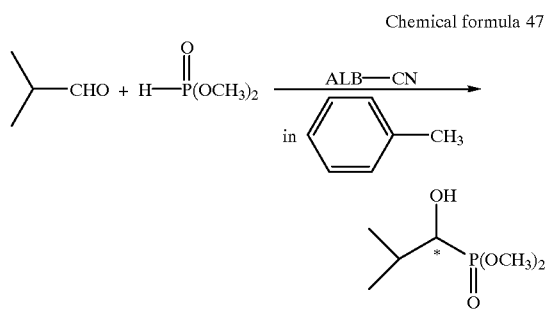

Chemical formula 47

The results of an analysis of this reaction product are shown in Table 36.

TABLE 36

| $^1$H NMR(CDCl$_3$) (δ) | 1.15.(dd, J=2.0, 6.9Hz, 6H), 2.19 (m, 1H), 2.95(t, J=6.6Hz, 1H), 3.79 (dd, J=9.3, 12.2Hz, 1H), 3.89 (d, J=10.6Hz, 3H), 3.90 (d, J=10.6Hz, 3H) |
|---|---|
| Optical purity (HPLC analysis) | 29% e.e. HPLC analysis conditions: CHIRALPAK AS manufactured by Daicel Chemical Industries Co., Ltd., isopropanol/hexane = 1/4, detection: differential refraction, flow rate: 0.5 ml/min. |

EXAMPLE 43

Asymmetric Hydrophosphonylation Reaction using ALB-CN

The same procedure as shown in Example 41 was used, except that 3-methyl-2-butenal was used in place of the p-methoxybenzaldehyde used in Example 41 to afford dimethyl (R)-1-hydroxy-3-methyl-2-butenylphosphonate as a final product in a yield of 34%. The chemical reaction in this Example is shown in chemical formula 48.

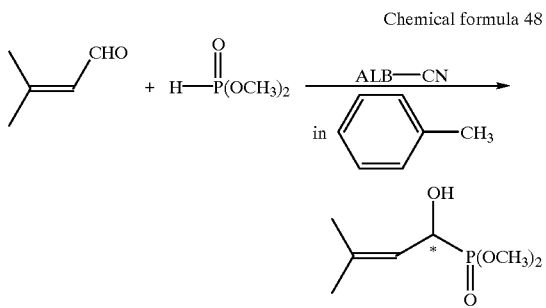

Chemical formula 48

The results of an analysis of this reaction product are shown in Table 37.

TABLE 37

| $^1$H NMR (CDCl$_3$) ($\delta$) | 1.71(dd, J=1.3, 3.0Hz, 3H), 1.81 (dd, J=1.0, 4.0Hz, 3H), 3.18(bs, 1H), 3.80(d, J=10.5Hz, 3H), 3.82 (d, J=10.5Hz, 3H), 4.66 (dt, 5.5, 9.1, 9.2, 1H), 5.33(m, 1H) |
|---|---|
| Optical purity (HPLC analysis) | 47% e.e. HPLC analysis conditions: CHIRALPAK AS manufactured by Daicel Chemical Industries Co., Ltd., isopropanol/hexane = 5/95, detection: differential refraction, flow rate: 0.5 ml/min. |

REFERENCE EXAMPLE

Reduction of Unsaturated Bond

Dimethyl (S)-1-hydroxy-3-methyl-2-butenylphosphonate obtained in Example 31 (68% e.e., 54 mg) was dissolved in 10 ml of methanol, and 10% Pd/C (16 mg) was added thereto. The mixture was stirred at room temperature for 3 hours under hydrogen atmosphere. The reaction mixture was filtered through Celite and the filter cake was washed with ethyl acetate. The solvent was distilled under reduced pressure and the residue was purified by flash column chromatography (acetone/hexane=1/4, on SiO$_2$) to obtain dimethyl (S)-1-hydroxy-3-methylbutylphosphonate as a final product in a yield of 98%. This compound is known to be useful as a raw material for medicines and the like. The chemical reaction in this Reference Example is shown in chemical formula 49.

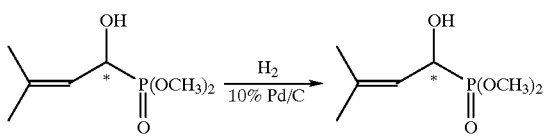

Chemical formula 49

The results of an analysis of this reaction product are shown in Table 38.

TABLE 38

| IR (neat) | 3320 cm$^{-1}$ |
|---|---|
| $^1$H NMR (CDCl$_3$) ($\delta$) | 0.90(d, J=6.6Hz, 3H), 0.95 (d, J=6.6Hz, 3H), 1.47(m, 1H), 1.73 (m.1H), 1.95(m, 1H), 3.78 |

TABLE 38-continued

| | (d, J=10.2Hz, 3H), 3.79 (d, J=10.2Hz, 3H), 4.00(m, 1H) |
|---|---|
| $^{13}$C NMR(CDCl$_3$) ($\delta$) | 21.0, 23.4, 24.0(J=14.6Hz), 39.9, 53.2(J=4.9Hz), 53.3(J=6.1Hz), 65.5(J=161.1Hz) |
| MS m/z | 196 (M$^+$) |
| $[\alpha]_D^{25}$ | +16.4° (c 1.0, CHCl$_3$) |
| Optical purity (HPLC analysis) | 68% e.e. HPLC analysis conditions: CHIRALPAK AS manufactured by Daicel Chemical Industries Co., Ltd., isopropanol/hexane = 1/4, flow rate: 1.0 ml/min., detection: differential refraction |

INDUSTRIAL APPLICABILITY

The process for producing an asymmetric compound of the present invention is suitable for obtaining, in a high yield, an optically active compound having high optical purity, which is useful as an intermediate for medicines, by an asymmetric Michael reaction and an asymmetric hydrophosphonylation reaction although the process uses, as a catalyst, a metal complex containing no rare earth metal element.

What is claimed is:

1. A metal complex produced by a reaction of (a) an optically active binaphthol or a derivative thereof, and (b) an alkali metal aluminum hydride or an alkali metal aluminum hydride compound, wherein the optically active binaphthol derivative is an optically active compound represented by the formula:

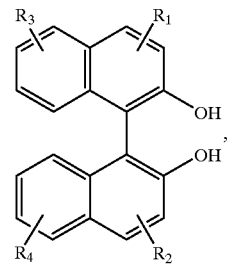

wherein R$_1$, R$_2$, R$_3$, and R$_4$, same or different, independently, are selected from the group consisting of hydrogen atom, lower alkyl group, lower alkoxy group, halogen, cyano, and nitro.

2. The metal complex according to claim 1 wherein a ratio of equivalents of the optically active binaphthol or a derivative thereof to equivalents of the alkali metal aluminum hydride or alkali metal aluminum hydride compound is 1–4:1.

3. A metal complex produced by a reaction of (a) an optically active binaphthol or a derivative thereof, (b) dialkylaluminum hydride, and (c) a base containing an alkali metal or an alkaline earth metal, wherein the optically active binaphthol derivative is an optically active compound represented by the formula:

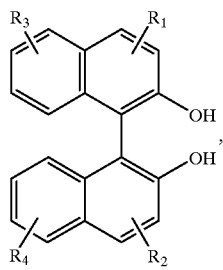

wherein $R_1$, $R_2$, $R_3$, and $R_4$, same or different, independently, are selected from the group consisting of hydrogen atom, lower alkyl group, lower alkoxy group, halogen, cyano, and nitro.

4. The metal complex according to claim 3 wherein a ratio of equivalents of the optically active binaphthol or a derivative thereof, the dialkylaluminum hydride, and the base containing an alkali metal or alkaline earth metal is 1–4:0.5–2:1.

5. A solution of a metal complex of claim 1 obtained by said reaction and an organic solvent.

6. The solution of a metal complex of claim 5 wherein the organic solvent is an ether compound.

7. The solution of a metal complex of claim 6 wherein the ether compound is selected from the group consisting of tetrahydrofuran, diethyl ether, methyl tert-butyl ether, dioxane, and mixtures thereof.

8. A solution or a metal complex of claim 2 obtained by said reaction and an organic solvent.

9. The solution of a metal complex of claim 8 wherein the organic solvent is an ether compound.

10. The solution of a metal complex of claim 9 wherein the ether compound is selected from the group consisting of tetrahydrofuran, diethyl ether, methyl tert-butyl ether, dioxane, and mixtures thereof.

* * * * *